(12) United States Patent
Mills

(10) Patent No.: US 6,362,191 B1
(45) Date of Patent: Mar. 26, 2002

(54) AMINOMETYL OXOOXAZOLIDINYL BENZENE DERIVATIVES

(75) Inventor: Stuart Dennett Mills, Macclesfield (GB)

(73) Assignee: Zeneca Ltd. (GB)

( * ) Notice: Subject to any disclaimer, the term of this patent is extended or adjusted under 35 U.S.C. 154(b) by 0 days.

(21) Appl. No.: 09/485,972

(22) PCT Filed: Aug. 25, 1998

(86) PCT No.: PCT/GB98/02556

§ 371 Date: Feb. 18, 2000

§ 102(e) Date: Feb. 18, 2000

(87) PCT Pub. No.: WO99/11642

PCT Pub. Date: Mar. 11, 1999

(30) Foreign Application Priority Data

Aug. 29, 1997 (GB) ................................ 9718208
Dec. 24, 1997 (GB) ................................ 9727160

(51) Int. Cl.$^7$ ..................... C07D 411/10; C07D 471/04; C07D 487/04; A61K 31/422; A61P 31/04
(52) U.S. Cl. ........................ 514/258; 514/299; 514/300; 514/368; 514/375; 514/376; 544/281; 546/112; 546/121; 548/126; 548/229
(58) Field of Search ................. 514/258, 299, 514/300, 368; 544/281; 546/112, 121; 548/126, 229

(56) References Cited

U.S. PATENT DOCUMENTS 4,942,183 A * 7/1990 Gregory et al. .......... 514/376

* cited by examiner

Primary Examiner—Richard L. Raymond
Assistant Examiner—Thomas C McKenzie
(74) Attorney, Agent, or Firm—Kenneth F. Mitchell

(57) ABSTRACT

The invention concerns compounds of formula (I),

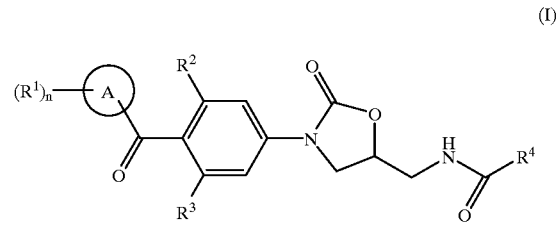

wherein:

A is a 5 membered heteroaryl ring, a bicyclic benzo system containing such a 5 membered heteroaryl ring or a bicyclic or tricyclic heteroaryl ring system with at least one bridgehead nitrogen and optionally a further 1–3 heteroatoms chosen from oxygen, sulfur and nitrogen;

$R^1$ is, for example, hydroxy, halo, amino, nitro, cyano, carboxy, thiol, $C_{1-4}$alkanoyloxy, $C_{1-4}$alkoxycarbonyl, dimethylaminomethyleneaminocarbonyl, $C_{1-4}$alkyl, $C_{2-4}$alkenyl, $C_{2-4}$alkynyl, $C_{1-4}$alkoxy, optionally substituted phenyl, an optionally substituted 5- or 6-membered heteroaryl ring or hydroxy$C_{1-4}$alkyl;

n is 0–6;

$R^2$ and $R^3$ are independently hydrogen or fluoro;

$R^4$ is, for example, $C_{1-4}$alkyl; pharmaceutically acceptable salts and in vivo hydrolysable ester thereof; processes for their preparation; pharmaceutical compositions containing them and their use as antibacterial agents.

15 Claims, No Drawings

AMINOMETYL OXOOXAZOLIDINYL BENZENE DERIVATIVES

The present invention relates to antibiotic compounds and in particular to antibiotic compounds containing an oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant staphylococcus (MRSA), methicillin resistant coagulase negative staphylococci (MRCNS), penicillin resistant streptococcus pneumoniae and multiply resistant Enterococcus faecium.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

The present inventor has discovered a class of antibiotic compounds containing an oxazolidinone ring which has useful activity against Gram-positive pathogens including MRSA and MRCNS and, in particular, against various strains exhibiting resistance to vancomycin and against *E. faecium* strains resistant to both aminoglycosides and clinically used β-lactams.

We have now discovered a range of compounds that have good activity against a broad range of Gram-positive pathogens including organisms known to be resistant to most commonly used antibiotics. In comparison with compounds described in the art (Walter A. Gregory et al, *J. Med. Chem.*, 1990, 33, 2569–2578 and Chung-Ho Park et al, *J. Med. Chem.*, 1992, 35, 1156–1165) the compounds also possess a favourable toxicological profile.

Accordingly the present invention provides a compound of formula (I),

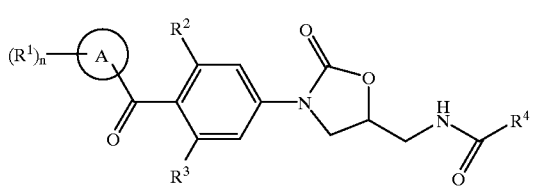

(I)

wherein:

A is linked via a ring carbon atom and is a 5 membered heteroaryl ring containing one nitrogen atom and optionally 1–3 further heteroatoms chosen from oxygen, sulfur and nitrogen, or a bicyclic benzo system containing such a 5 membered heteroaryl ring and is linked via a ring carbon atom in the 5 membered heteroaryl ring, or A is a bicyclic or tricyclic heteroaryl ring system with at least one bridgehead nitrogen and optionally a further 1–3 heteroatoms chosen from oxygen, sulfur and nitrogen and is linked via a ring carbon atom in a ring containing a bridgehead nitrogen;

$R^1$ is attached to a ring carbon atom and is hydroxy, halo, amino, nitro, cyano, carboxy, thiol, $C_{1-4}$alkanoyloxy, $C_{1-4}$alkoxycarbonyl, dimethylaminomethyleneaminocarbonyl, $C_{1-4}$alkyl, $C_{2-4}$alkenyl, $C_{2-4}$alkynyl, $C_{1-4}$alkoxy, $R^5$—, $R^5$—O—, $R^5$—$C_{1-4}$alkyl-, $R^5$—C(O)NH—, [where $R^5$ is optionally substituted phenyl, an optionally substituted 5- or 6-membered heteroaryl ring, an optionally substituted 5- or 6-membered heterocycle or an optionally substituted bicyclic heteroaryl ring], hydroxy$C_{1-4}$alkyl, carbamoyl, N—($C_{1-4}$alkyl)carbamoyl, N,N—($C_{1-4}$alkyl)$_2$carbamoyl, thiocarbamoyl, N—($C_{1-4}$alkyl)thiocarbamoyl, N,N—($C_{1-4}$alkyl)$_2$thiocarbamoyl, trifluoromethyl, $C_{1-4}$alkanoylamino [where the $C_{1-4}$alkanoyl group is optionally substituted by hydroxy], $R^6$-thio, $R^6$-sulfinyl, $R^6$-sulfonyl [where $R^6$ is $C_{1-4}$alkyl optionally substituted by one or more groups independently selected from cyano, hydroxy and $C_{1-4}$alkoxy], $C_{1-4}$alkanoyl, sulfonamido, $C_{1-4}$alkylamino, di($C_{1-4}$alkyl)amino, $C_{1-4}$alkoxy$C_{1-4}$alkyl, carbamoyl$C_{1-4}$alkyl or cyanoamino, or $R^1$ is attached to a ring nitrogen atom where such substitution does not result in quaternization and is selected from $R^7$—, $R^7$—C(O)— [where $R^7$ is $C_{1-4}$alkyl optionally substituted by cyano, hydroxy or $C_{1-4}$alkoxyl] or $C_{1-4}$alkoxyC(O)—;

n is 0–6;

$R^2$ and $R^3$ are independently hydrogen or fluoro;

$R^4$ is hydrogen, $C_{1-4}$alkyl, $C_{1-4}$alkoxy, amino, chloromethyl, dichloromethyl, cyanomethyl, methoxymethyl, acetylmethyl, methylamino and dimethylamino; or a pharmaceutically acceptable salt or in vivo hydrolysable ester thereof.

In this specification the term 'alkyl' includes straight chained, branched structures and ring systems. For example, $C_{1-4}$alkyl includes methyl ethyl, propyl, isopropyl, t-butyl, cyclopropane and cyclobutane; $C_{1-6}$alkyl includes methyl, ethyl, propyl, isopropyl. t-butyl, cyclopropane and cyclohexane. However, references to individual alkyl groups such as 'propyl' are specific for the straight chained version only, references to individual branched chain alkyl groups such as 'isopropyl' are specific for the branched chain version only and references to the cyclo groups such as cyclohexane are specific to the cyclic groups only.

A similar convention applies to other radicals, for example "hydroxy$C_{1-4}$alkyl" includes 1-hydroxyethyl and 2-hydroxyethyl.

The term "halo" refers to fluoro, chloro, bromo and iodo.

"Aryl" means phenyl or naphthyl.

"Heteroaryl" means, unless otherwise further specified, a monocyclic-, bicyclic- or tricyclic-5–14 membered ring that contains some degree of unsaturation, with up to five ring heteroatoms selected from nitrogen, oxygen and sulfur. Examples of "heteroaryl" include thienyl, furanyl, imidazolyl, thiazolyl, pyrimidinyl, pyridinyl, indolyl, benzimidazolyl, benzthiazolyl, quinolyl, isoquinolinyl, xanthene, phenoxathiin and chromene. Examples of a 5 membered heteroaryl ring containing one nitrogen atom and optionally 1–3 further heteroatoms chosen from oxygen, sulfur and nitrogen include pyrrole, imidazole, triazole, thiazole and isoxazole. Examples of a bicyclic benzo system containing a 5 membered heteroaryl ring containing one nitrogen atom and optionally 1–3 further heteroatoms chosen from oxygen, sulfur and nitrogen include indole, benzothiazole and benzimidazole. Examples of bicyclic or tricyclic heteroaryl ring system with at least one bridgehead nitrogen and optionally a further 1–3 heteroatoms chosen from oxygen, sulfur and nitrogen include 3H-pyrrolo[1,2-a]-pyrrole, pyrrolo[2,1-b]thiazole, 1H-imidazo[1,2-a]pyrrole, 1H-imidazo[1,2-a]imidazole, 1H-pyrrolo[1,2-a]benzimidazole, 9H-imidazo[1,2-a]indole, 5H-imidazo[2,1-a]isoindole, 1H,3H-pyrrolo[1,2-c]oxazole, 1H-imidazo[1,5-a]pyrrole, 1H-imidazo[3,4-a]indole, pyrrolo[1,2-b]isoxazole, imidazo[5,1-b]thiazole, imidazo[2,1-b]thiazole, indolizine, pyrrolo[a]quinoline, 2,3-pyrroloisoquinoline, pyrrolo[a]isoquinoline, imidazo[1,2-a]pyridine, imidazo[1,2-a]quinoline, imidazo[2,1-a]isoquinoline, imidazo[1,5-a]pyridine, imidazo[1,5-a]quinoline, imidazo[5,1-a]isoquinoline, pyrazolo[1,5-a]pyridine, pyrrolo[1,2-b]pyridazine, pyrrolo [1,2-c]pyrimidine, pyrrolo[1,2-a]pyrazine, pyrrolo[1,2-a]pyrimidine, pyrido[2,1-c]-s-triazole, s-triazole[1,5-a]pyridine, imidazo[2,1-c]pyrimidine, imidazo[1,2-a]pyrazine, imidazo[1,2-a]pyrimidine, imidazo[1,5-a]pyrazine, imidazo[1,5-a]pyrimidine, imidazo[1,2-b]-pyridazine, s-triazolo[4,3-a]pyrimidine, imidazo[5,1-b]oxazole and imidazo[2,1-b]oxazole; and partially saturated versions thereof. The nomenclature used is that found in "Heterocyclic Compounds (Systems with bridgehead nitrogen), W. L. Mosby (Intercsience Publishers Inc., New York), 1961, Parts 1 and 2. Some of the above ring systems are illustrated hereinafter.

"Heterocycle" means a mono- or bicyclic-5–10 membered ring, that is totally saturated, with up to five ring heteroatoms selected from nitrogen, oxygen and sulfur. Examples of such heterocycles include morpholine, pyrrolidine, piperazine, imidazoline and piperidine.

Suitable optional substituents for $R^5$ include all of the values of $R^1$ except where $R^1$ includes an $R^5$ group.

An example of "$C_{1-4}$alkanoyloxy" is acetoxy. Examples of "$C_{1-4}$alkoxycarbonyl" include methoxycarbonyl, ethoxycarbonyl, n- and t-butoxycarbonyl. Examples of "$C_{1-4}$alkyl" include methyl, ethyl, propyl, isopropyl and t-butyl. Examples of "$C_{2-4}$alkenyl" include ethenyl and 1-propenyl. Examples of "$C_{2-4}$alkynyl" ethynyl and 2-propynyl. Examples of "$C_{1-4}$alkoxy" include methoxy, ethoxy and propoxy. Examples of hydroxy $C_{1-4}$ alkyl include hydroxymethyl and 2-hydroxyethyl. Examples of "N—($C_{1-4}$alkyl)carbamoyl" include N-methylcarbamoyl, N-ethylcarbamoyl and N-propylcarbamoyl. Examples of "N,N—($C_{1-4}$alkyl)$_2$carbamoyl" include N,N-dimethylcarbamoyl and N,N-diethylcarbamoyl. Examples of "N—($C_{1-4}$alkyl)thiocarbamoyl" include N-methylthiocarbamoyl. N-ethylthiocarbamoyl and N-propylthiocarbamoyl. Examples of "N,N—($C_{1-4}$alkyl)$_2$thiocarbamoyl" include N,N-dimethylthiocarbamoyl and N,N-diethylthiocarbamoyl. Examples of "$C_{1-4}$alkanoylamino" include formamido, acetamido and propionylamino. Examples of "$C_{1-4}$alkylthio" (where the $C_{1-4}$alkyl is optionally substituted by cyano, hydroxy or $C_{1-4}$alkoxy) include methylthio, 2-hydroxyethylthio, 2,3-dihydroxypropylthio and methoxyethylthio. Examples of "$C_{1-4}$alkylsulfinyl" (where the $C_{1-4}$alkyl is optionally substituted by cyano, hydroxy or $C_{1-4}$alkoxy) include methyl-sulfinyl 2-hydroxyethylsulfinyl and methoxyethylsulfinyl. Examples of "$C_{1-4}$alkylsulfonyl" (where the $C_{1-4}$alkyl is optionally substituted by cyano, hydroxy or $C_{1-4}$alkoxy) include methylsulfonyl 2-hydroxyethylsulfonyl and methoxyethylsulfonyl. Examples of "$C_{1-4}$alkanoyl" include propanoyl and ethanoyl. Examples of "$C_{1-4}$alkylamino" include methylamino and ethylamino. Examples of "di($C_{1-4}$alkyl)amino" include di-N-methylamino, di-(N-ethyl)amino and N-ethyl-N-methylamino. Examples of "$C_{1-4}$alkoxy$C_{1-4}$alkyl" methoxymethyl and propoxyethyl. Examples of "carbamoyl$C_{1-4}$alkyl" are methylcarboxamide and ethylcarboxamide.

The skilled man will appreciate that in this specification quarternization means a ring nitrogen atom with no replaceable hydrogen becoming positively charged by further substitution, by, for example, alkyl or amino.

Suitable pharmaceutically acceptable salts include acid addition salts such as methanesulfonate, fumarate, hydrochloride, hydrobromide, citrate, maleate and salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred pharmaceutically acceptable salt is a sodium salt.

However, to facilitate isolation of the salt during preparation, salts which are less soluble in the chosen solvent may be preferred whether pharmaceutically-acceptable or not.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl, 1,3-dioxolen-2-onylmethyl esters for example 5-methyl-1,3-dioxolen-2-onylmethyl and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters) dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

As a further feature of the invention there are provided suitable N-oxides of a compound of formula (I). Such N-oxides can be formed on an available ring nitrogen atom by, for example, reaction of the parent compound with an oxidizing agent such as metachloro-perbenzoic acid.

In another aspect there are provided compounds of formula (I) as described above, but wherein $R^1$ when it is $C_{1-4}$alkanoylamino is not optionally substituted by hydroxy in the $C_{1-4}$alkanoyl group; and where $R^6$ is $C_{1-4}$alkyl optionally substituted by cyano, hydroxy or $C_{1-4}$alkoxy.

In another aspect there are provided compounds of formula (I) as described anywhere above, but wherein $R^1$ is not dimethylaminomethyleneaminocarbonyl.

Particularly preferred compounds of the invention comprise a compound of formula (I), or a pharmaceutically-acceptable salt or in vivo hydrolysable ester thereof, wherein $R^1$, $R^2$, $R^3$, $R^4$, A and n have the values disclosed hereinbefore, or any of the following values:

Suitably $R^5$ is monosubstituted by any of the values for $R^1$ (excluding those where $R^1$ includes an $R^5$ group). Preferably $R^5$ is unsubstituted.

$R^1$ is preferably halo in particular fluoro, chloro or bromo.

$R^1$ is also preferably amino, (1–4C)alkyl, (1–4C) alkanoylamino (optionally substituted by hydroxy) cyano, nitro, trifluoromethyl, benzyloxy, (1–4C)alkoxycarbonyl, phenyl, hydroxy. dimethylaminomethyleneaminocarbonyl, (1–4C)alkylthio (optionally substituted by one or two hydroxy groups), (1–4C)alkylsulfinyl, (1–4C)alkylsulfonyl or hydroxy-(1–4C)alkyl.

In one aspect of the invention, preferably at least one of $R^2$ and $R^3$ are hydrogen, in particular one of $R^2$ or $R^3$ is hydrogen and the other is fluoro. In another aspect of the invention preferably both $R^2$ and $R^3$ are fluoro, or both are hydrogen.

$R^4$ is preferably hydrogen or $C_{1-4}$alkyl, in particular $C_{1-4}$alkyl, preferably methyl and ethyl and especially methyl.

When ring A is a bicyclic or tricyclic ring system it preferably has one bridgehead nitrogen and optionally a further 1–3 heteroatoms chosen from sulfur and nitrogen, especially nitrogen.

Ring A is preferably a 5,5- or 5,6-fused ring system with at least one bridgehead nitrogen. When ring A is a 5,6-ring system it is preferably an imidazopyridine ring system, in particular imidazo[1,2-a]pyridine or imidazo[1,5-a] pyridine, especially imidazo[1,2-a]pyridine. Also preferred are imidazopyrimidine ring systems, for example imidazo [1,2-c]pyrimidine, imidazo[1,2-a]pyrimidine and imidazol [1,5-a]pyrimidine, especially imidazo[1,2-a]pyrimidine. Preferably such ring systems are linked in the 3-position to the carbonyl group. When A is a 5,5-ring system it is preferably an imidazooxazole or imidazothiazole ring system, in particular imidazo[5,1-b]thiazole, imidazo[2,1-b] thiazole, imidazo[5,1-b]oxazole or imidazo[2,1-b]oxazole, especially imidazo[5,1-b]thiazole or imidazo[2,1-b]thiazole.

Preferably n is 1 or 0, particularly 1.

Therefore a preferred class of compounds is that of formula (I'):

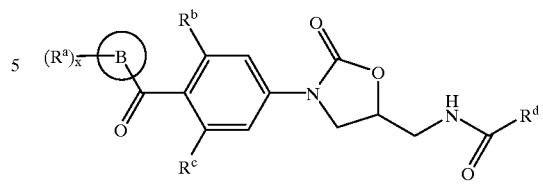

wherein:

$R^a$ is halo, amino, (1–4C)alkyl, (1–4C)alkanoylamino (optionally substituted by hydroxy) cyano, nitro, trifluoromethyl, benzyloxy, (1–4C)alkoxycarbonyl, phenyl, hydroxy, dimethylaminomethyleneaminocarbonyl, (1–4C) alkylthio (optionally substituted by one or two hydroxy groups), (1–4C)alkylsulfinyl, (1–4C)alkylsulfonyl, hydroxy-(1,4C)alkyl, [especially halo];

$R^b$ is hydrogen or fluoro;

$R^c$ is hydrogen or fluoro;

$R^d$ is $C_{1-4}$alkyl;

B is a 5,5- or 5,6- fused ring system with at least one bridgehead nitrogen;

x is 0 or 1 or 2 [especially 0 or 1];

or a pharmaceutically acceptable salt or in vivo hydrolysable ester thereof.

Of the above compounds of formula (I'), preferred values of $R^a$, $R^b$, $R^c$, $R^d$, B and x are as follows:

Preferably $R^a$ is halo, especially fluoro, chloro or bromo.

In one aspect of the invention, preferably at least one of $R^c$ and $R^b$ are hydrogen, in particular one of $R^c$ or $R^b$ is hydrogen and the other is fluoro. In another aspect of the invention preferably both $R^c$ and $R^b$ are fluoro, or both are hydrogen.

Preferably $R^d$ is methyl. Preferably x is 0 or 1, especially 1.

When B is a 5,6-fused ring system with a bridgehead nitrogen it is preferably an imidazopyridine ring system, in particular imidazo[1,2-a]pyridine or imidazo[1,5-a] pyridine, especially imidazo[1,2-a]pyridine. Also preferred are imidazopyrimidine ring systems, for example imidazo [1,2-c]pyrimidine, imidazo [1,2-a]pyrimidine and imidazo [1,5-a]pyrimidine, especially imidazo[1,2-a]pyrimidine. Preferably such ring systems are linked in the 3-position to the carbonyl group. When B is a 5,5-fused ring system with a bridgehead nitrogen it is preferably an imidazooxazole or imidazothiazole ring system, in particular imidazo[5,1-b] thiazole, imidazo [2,1-b]thiazole, imidazo[5,1-b]oxazole or imidazo[2,1-b]oxazole, especially imidazo[5,1-b]thiazole or imidazo[2,1-b]thiazole linked via the imidazo ring preferably in the position ortho to the bridgehead nitrogen.

The naming and numbering systems of the heteroaryl rings referred to in this specification is that found in "Heterocyclic Compounds (Systems with bridgehead nitrogen), W. L. Mosby (Intercsience Publishers Inc., New York), 1961, Parts 1 and 2, and is illustrated, but not limited by the following:

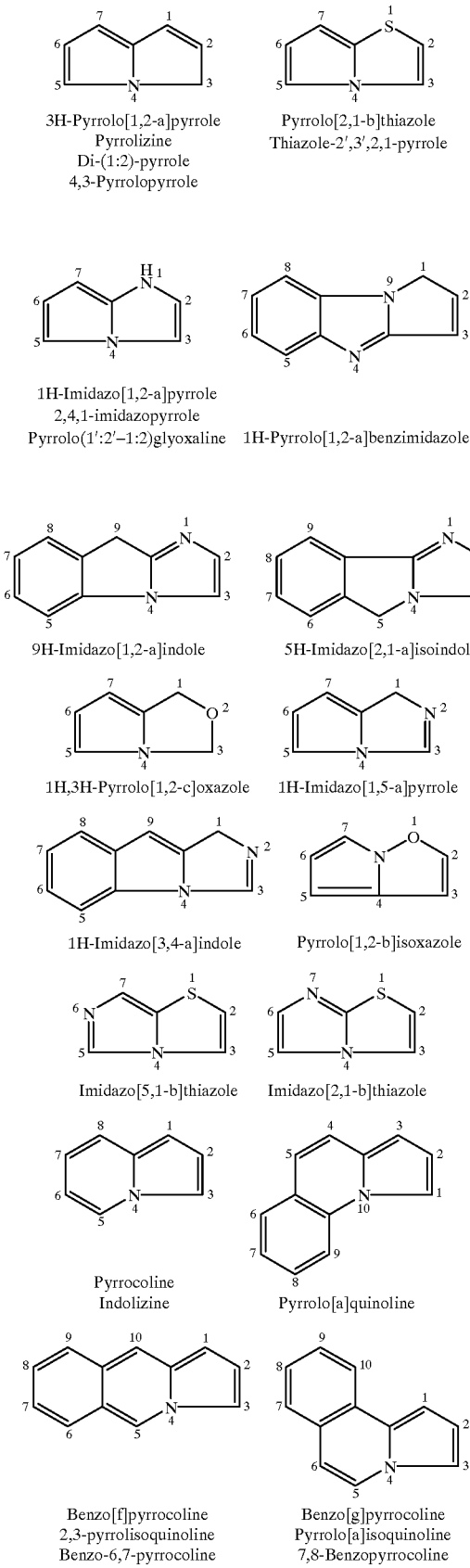
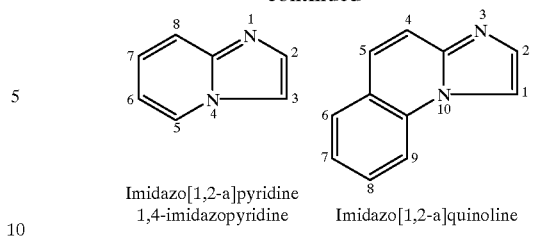
The naming and numbering systems of the heteroaryl rings referred to in this specification is further illustrated, but not limited by the following:
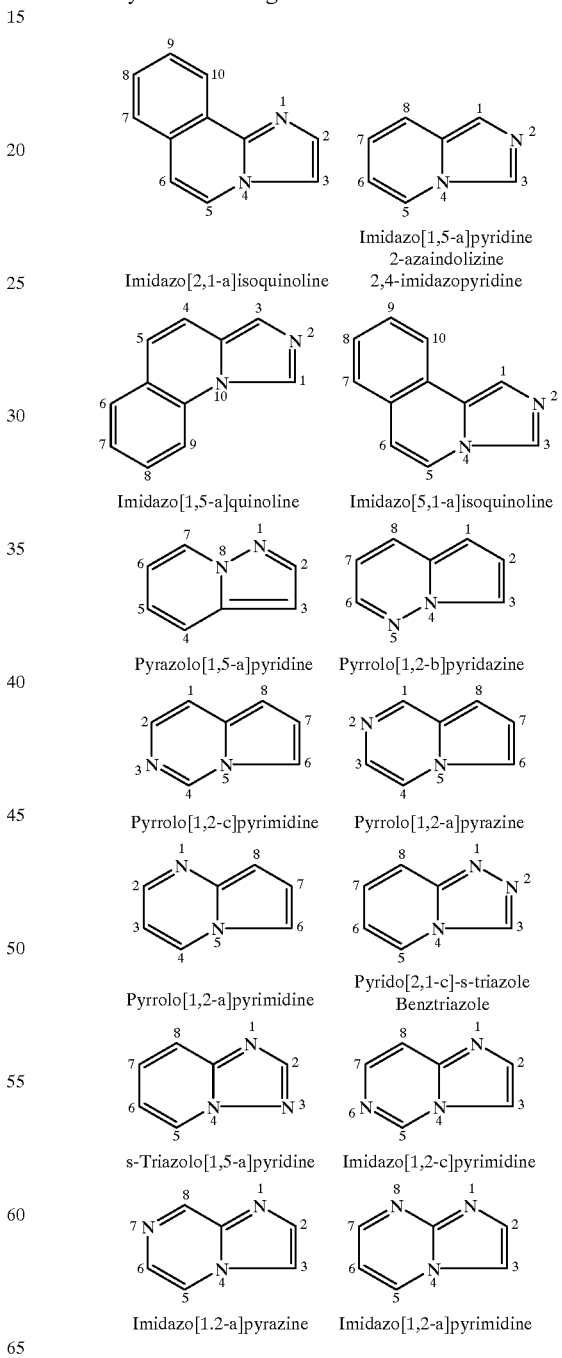

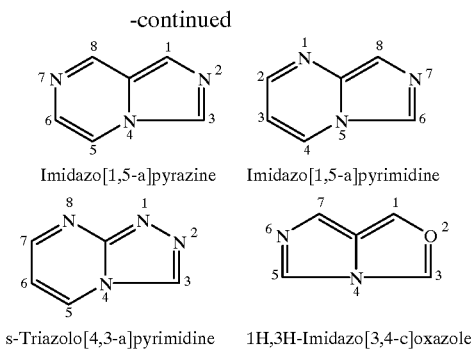

Imidazo[1,5-a]pyrazine   Imidazo[1,5-a]pyrimidine s-Triazolo[4,3-a]pyrimidine   1H,3H-Imidazo[3,4-c]oxazole Preferred compounds having formula (I) include the following (in which the nomenclature used hereinafter refers to the phenyl moiety being linked to the N-position of oxazolidinone ring; an alternative, equivalent, nomenclature would refer to the phenyl moiety being linked to the 3-position of oxazolidinone ring):

N-([(5S)-N-(4-[indolin-3-ylcarbonyl]phenyl)-2-oxooxazolidin-5-yl]methyl)acetamide;
N-([(5S)-N-(4-[6-methylindolizin-3-ylcarbonyl]phenyl)-2-oxooxazolidin-5-yl]methyl)acetamide;
N-([(5S)-N-(4-[6-cyanoindolizin-3-ylcarbonyl]phenyl)-2-oxooxazolidin-5-yl]methyl)acetamide;
N-([(5S)-N-(4-[3-methylpyrrolo[1,2-a]pyrazin-6-ylcarbonyl]phenyl)-2-oxo oxazolidin-5-yl]methyl)acetamide;
N-([(5S)-N-(4-[imidazo[1,2-a]pyridin-3-ylcarbonyl]phenyl)-2-oxooxazolidin-5-yl]methyl)acetamide;
N-([(5S)-N-(4-[imidazo[1,2-a]pyrimidin-3-ylcarbonyl]phenyl)-2-oxooxazolidin-5-yl]methyl)acetamide;
N-([(5S)-N-(4-[5,7-dimethylimidazo[1,2-a]pyrimidin-3-ylcarbonyl]phenyl)-2-oxooxazolidin-5-yl]methyl)acetamide;
N-([(5S)-N-(4-[6-bromoimidazo[1,2-a]pyridin-3-ylcarbonyl]phenyl)-2-oxooxazolidin-5-yl]methyl)acetamide;
N-([(5S)-N-(4-[imidazo[2,1-a]isoquinol-3-ylcarbonyl]phenyl)-2-oxooxazolidin-5-yl]methyl)acetamide.
N-([(5S)-N-(4-[imidazo[2,1-b]thiazol-5-ylcarbonyl]phenyl)-2-oxooxazolidin-5-yl]methyl)acetamide;
N-([(5S)-N-(4-[6,8-dichloroimidazo[1,2-a]pyridin-3-ylcarbonyl]phenyl)-2-oxooxazolidin-5-yl]methyl)acetamide;
N-([(5S)-N-(4-[1-cyanoindolizin-3-ylcarbonyl]phenyl)-2-oxooxazolidin-5-yl]methyl)acetamide;
N-([(5S)-N-(4-[7-methylimidazo[1,2-a]pyridin-3-ylcarbonyl]phenyl)-2-oxooxazolidin-5-yl]methyl)acetamide;
N-([(5S)-N-(4-[6-chloroimidazo[1,2-a]pyridin-3-ylcarbonyl]phenyl)-2-oxooxazolidin-5-yl]methyl)acetamide;
N-([(5S)-N-(4-[6-nitroimidazo[1,2-a]pyridin-3-ylcarbonyl]phenyl)-2-oxooxazolidin-5-yl]methyl)acetamide;
N-([(5S)-N-(4-[8-nitroimidazo[1,2-a]pyridin-3-ylcarbonyl]phenyl)-2-oxooxazolidin-5-yl]methyl)acetamide;
N-([(5S)-N-(4-[5,7-dimethylimidazo[1,2-a]pyridin-3-ylcarbonyl]phenyl)-2-oxooxazolidin-5-yl]methyl)acetamide;
N-([(5S)-N-(4-[5-methylimidazo[1,2-a]pyridin-3-ylcarbonyl]phenyl)-2-oxooxazolidin-5-yl]methyl)acetamide;
N-([(5S)-N-(4-[8-bromo-6-methylimidazo[1,2-a]pyridin-3-ylcarbonyl]phenyl)-2-oxooxazolidin-5-yl]methyl)acetamide;
N-([(5S)-N-(4-[8-benzyloxyimidazo[1,2-a]pyridin-3-ylcarbonyl]phenyl)-2-oxooxazolidin-5-yl]methyl)acetamide;
N-([(5S)-N-(4-[6-trifluoromethylimidazo[1,2-a]pyridin-3-ylcarbonyl]phenyl)-2-oxooxazolidin-5-yl]methyl)acetamide;
N-([(5S)-N-(4-[imidazo[1,2-a]pyridin-3-ylcarbonyl]{3-fluorophenyl})-2-yl]methyl)acetamide;
N-([(5S)-N-(4-[8-methoxycarbonylimidazo[1,2-a]pyridin-3-ylcarbonyl]phenyl)-2-oxooxazolidin-5-yl]methyl)acetamide;
N-([(5S)-N-(4-[6-methoxycarbonylimidazo[1,2-a]pyridin-3-ylcarbonyl]phenyl)-2-oxooxazolidin-5-yl]methyl)acetamide;
N-([(5S)-N-(4-[7-phenylimidazo[1,2-a]pyridin-3-ylcarbonyl]phenyl)-2-oxooxazolidin-5-yl]methyl)acetamide;
N-([(5S)-N-(4-[8-hydroxyimidazo[1,2-a]pyridin-3-ylcarbonyl]phenyl)-2-oxooxazolidin-5-yl]methyl)acetamide;

or a pharmaceutically acceptable salt or in vivo hydrolysable ester thereof.

Further preferred compounds having formula (I) include:

N-([(5S)-N-(4-[imidazo[2,1-b]oxazol-5-ylcarbonyl]phenyl)-2-oxooxazolidin-5-yl]methyl)acetamide;
N-([(5S)-N-(4-[1-methylimidazo[1,2-a]pyrrol-5-ylcarbonyl]phenyl)-2-oxooxazolidin-5-yl]methyl)acetamide;
N-([(5S)-N-(4-[6-cyanoimidazo[1,2-a]pyridin-3-ylcarbonyl]phenyl)-2-oxooxazolidin-5-yl]methyl)acetamide;
N-([(5S)-N-(4-[pyrrol-2-ylcarbonyl]phenyl)-2-oxooxazolidin-5-yl]methyl)acetamide;
N-([(5S)-N-(4-[1-hydroxymethylcarbonylpyrrol-2-ylcarbonyl]phenyl)-2-oxooxazolidin-5-yl]methyl)acetamide;
N-([(5S)-N-(4-[imidazol-2-ylcarbonyl]phenyl)-2-oxooxazolidin-5-yl]methyl)acetamide;
N-([(5S)-N-(4-[1-hydroxymethylcarbonylimidazol-2-ylcarbonyl]phenyl)-2-oxooxazolidin-5-yl]methyl)acetamide;
N-([(5S)-N-(4-[imidazo[1,2-a]pyridin-2-ylcarbonyl]phenyl)-2-oxooxazolidin-5-yl]methyl)acetamide;
N-([(5S)-N-(4-[imidazo[2,1-b]thiazol-5-ylcarbonyl]{3-fluorophenyl})-2-oxooxazolidin-5-yl]methyl)acetamide;

or a pharmaceutically acceptable salt or in vivo hydrolysable ester thereof.

Yet further preferred compounds having formula (I) include:

N-([(5S)-N-(4-[6-fluoroimidazo[1,2-a]pyridin-3-ylcarbonyl]phenyl)-2-oxooxazolidin-5-yl]methyl)acetamide;
N-([(5S)-N-(4-[6-cyanoimidazo[1,2-a]pyridin-3-ylcarbonyl]phenyl)-2-oxooxazolidin-5-yl]methyl)acetamide;
N-([(5S)-N-(4-[1-methylimidazo[1,2-a]imidazol-5-ylcarbonyl]phenyl)-2-oxooxazolidin-5-yl]methyl)acetamide;
N-([(5S)-N-(4-[2.3-dihydroimidazo[2,1-b]thiazol-5-ylcarbonyl]phenyl)-2-oxooxazolidin-5-yl]methyl)acetamide;

N-([(5S)-N-(4-[6-{dimethylaminomethyleneaminocarbonyl}imidazo[1,2-a]pyridin-3-ylcarbonyl]phenyl)-2-oxooxazolidin-5-yl] methyl)acetamide;
N-([(5S)-N-(4-[thiazol-2-ylcarbonyl]phenyl)-2-oxooxazolidin-5-yl]methyl)acetamide;
N-([(5S)-N-(4-[benzothiazol-2-ylcarbonyl]phenyl)-2-oxooxazolidin-5-yl]methyl)acetamide;

or a pharmaceutically acceptable salt thereof.

Yet further preferred compounds having formula (I) include:

N-([(5S)-N-(4-[6-aminoimidazo[1,2-a]pyridin-3-ylcarbonyl]phenyl)-2-oxooxazolidin-5-yl]methyl)acetamide;
N-([(5S)-N-(4-[6-acetamidoimidazo[1,2-a]pyridin-3-ylcarbonyl]phenyl)-2-oxooxazolidin-5-yl]methyl)acetamide;
N-([(5S)-N-(4-[6-(hydroxyacetamido)imidazo[1,2-a]pyridin-3-ylcarbonyl]phenyl)-2-oxooxazolidin-5-yl]methyl)acetamide;
N-([(5S)-N-(4-[6-methylthioimidazo[1,2-a]pyridin-3-ylcarbonyl]phenyl)-2-oxooxazolidin-5-yl]methyl)acetamide;
N-([(5S)-N-(4-[6-(methylsulfinyl)imidazo[1,2-a]pyridin-3-ylcarbonyl]phenyl)-2-oxooxazolidin-5-yl]methyl)acetamide;
N-([(5S)-N-(4-[6-(methylsulfonyl)imidazo[1,2-a]pyridin-3-ylcarbonyl]phenyl)-2-oxooxazolidin-5-yl]methyl)acetamide;
N-([(5S)-N-(4-[6-(2-hydroxyethylthio)imidazo[1,2-a]pyridin-3-ylcarbonyl]phenyl)-2-oxooxazolidin-5-yl]methyl)acetamide;
N-([(5S)-N-(4-[6-(2,3-dihydroxypropylthio)imidazo[1,2-a]pyridin-3-ylcarbonyl]phenyl)-2-oxooxazolidin-5-yl]methyl)acetamide;
N-([(5S)-N-(4-[6-hydroxymethylimidazo[1,2-a]pyridin-3-ylcarbonyl]phenyl)-2-oxooxazolidin-5-yl]methyl)acetamide;
N-([(5S)-N-(4-[6-bromoimidazo[1,2-a]pyrazin-3-ylcarbonyl]phenyl)-2-oxooxazolidin-5-yl]methyl)acetamide;
N-([(5S)-N-(4-[6-chloroimidazo[1,2-b]pyridazine-3-ylcarbonyl]phenyl)-2-oxooxazolidin-5-yl]methyl)acetamide;
N-([(5S)-N-(4-[imidazo[1,2-a]pyrazin-3-ylcarbonyl]phenyl)-2-oxooxazolidin-5-yl]methyl)acetamide;
N-([(5S)-N-(4-[6-chloroimidazo[1,2-a]pyrimidin-3-ylcarbonyl]phenyl)-2-oxooxazolidin-5-yl]methyl)acetamide;
N-([(5S)-N-(4-[pyrrol-2-ylcarbonyl]phenyl)-2-oxooxazolidin-5-yl]methyl)acetamide;
N-([(5S)-N-(4-[1-methylpyrrol-2-yl carbonyl]phenyl)-2-oxooxazolidin-5-yl]methyl)acetamide;
N-([(5S)-N-(4-[imidazol-2-ylcarbonyl]phenyl)-2-oxooxazolidin-5-yl]methyl)acetamide;
N-([(5S)-N-(4-[1-methylimidazol-2-ylcarbonyl]phenyl)-2-oxooxazolidin-5-yl]methyl)acetamide; or a pharmaceutically acceptable salt thereof.

Especially preferred compounds having formula (I) are:

N-([(5S)-N-(4-[6-fluoroimidazo[1,2-a]pyridin-3-ylcarbonyl]phenyl)-2-oxooxazolidin-5-yl]methyl)acetamide;
N-([(5S)-N-(4-[6-chloroimidazo[1,2-a]pyridin-3-ylcarbonyl]phenyl)-2-oxooxazolidin-5-yl]methyl)acetamide; or a pharmaceutically acceptable salt thereof.

Further especially preferred compounds having formula (I) are:

N-([(5S)-N-(4-[imidazo[1,2-a]pyrazin-3-ylcarbonyl] phenyl)-2-oxooxazolidin-5-yl methyl)acetamide;
N-([(5S)-N-(4-[6-chloroimidazo[1,2-a]pyrimidin-3-ylcarbonyl]phenyl)-2-oxooxazolidin-5-yl]methyl) acetamide;
N-([(5S)-N-(4-[6-(2-hydroxyethylthio)imidazo[1,2-a] pyridin-3-ylcarbonyl]phenyl)-2-oxooxazolidin-5-yl] methyl)acetamide;
N-([(5S)-N-(4-[6-fluoroimidazo[1,2-a]pyridin-3-ylcarbonyl]phenyl)-2-oxooxazolidin-5-yl)methyl) acetamide;
N-([(5S)-N-(4-[imidazo[1,2-a]pyridin-3-ylcarbonyl]{3-fluorophenyl})-2-oxooxazolidin-5-yl]methyl)acetamide;
N-([(5S)-N-(4-[6-chloroimidazo[1,2-a]pyridin-3-ylcarbonyl]phenyl)-2-oxooxazolidin-5-yl]methyl) acetamide;
N-([(5S)-N-(4-[imidazo[2,1-b]thiazol-5-ylcarbonyl] phenyl)-2-oxooxazolidin-5-yl]methyl)acetamide;
N-([(5S)-N-(4-[6-bromoimidazo[1,2-a]pyridin-3-ylcarbonyl]phenyl)-2-oxooxazolidin-5-yl]methyl) acetamide.

Also especially preferred is the compound of formula (I) being:

N-([(5S)-N-(4-[6-fluoroimidazo[1,2-a]pyrimidin-3-ylcarbonyl]phenyl)-2-oxooxazolidin-5-yl]methyl) acetamide.

The compounds of the present invention have a chiral centre at the C-5 position of the oxazolidinone ring. The pharmaceutically active enantiomer is of formula (IA):

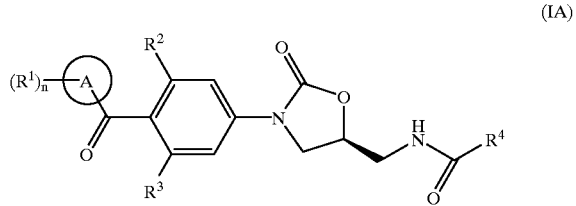

(IA)

The present invention includes the pure 5S enantiomer depicted above or mixtures of the 5R and 5S enantiomers, for example a racemic mixture. In a pharmaceutical composition if a mixture of enantiomers is used, a larger amount (depending upon the ratio of the enantiomers) will be required to achieve the same effect as the same weight of the pharmaceutically active enantiomer.

Some compounds of formula (I) may possess other chiral centres. It is to be understood that the invention encompasses all such optical isomers and diastereoisomers of compounds of formula (I).

The invention further relates to all tautomeric forms of the compounds of formula (I) that possess antibacterial activity.

It is also to be understood that certain compounds of the formula (I) can exist in solvated as well as unsolvated forms such as, for example, hydrated forms. It is to be understood that the invention encompasses all such solvated forms that possess antibacterial activity.

Another aspect of the present invention provides a process for preparing a compound of formula (I), or a pharmaceutically acceptable salt or an in vivo hydrolysable ester thereof (where $R^1$, $R^2$, $R^3$, $R^4$ and n are as defined for formula (I) which comprises the following processes (a) to (i):

a) reacting a compound of formula (II)

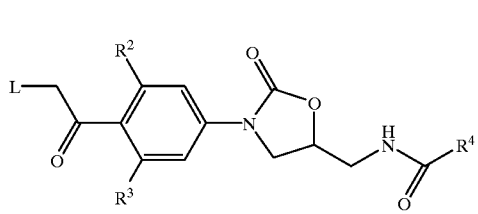
(II)

where L is a leaving group, with a compound of formula (III)

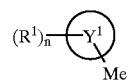
(III)

where $Y^1$ is a mono- or bicyclic-heteroaryl ring containing at least one nitrogen atom that is capable of quaternizing with (II) and the Me group is ortho to this nitrogen, in the presence of dimethylformamide dimethylacetal (DMFDMA) (IV)

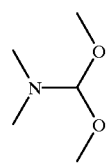
(IV)

to give a compound of formula (V)

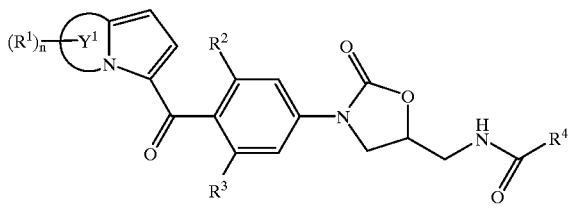
(V)

b) reacting a compound of formula (II) with a compound of formula (VI)

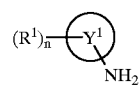
(VI)

where $Y^1$ is as defined above and the $NH_2$ group is ortho to the nitrogen that is capable of quaternizing with (II), in the presence of DMFDMA (IV) to give a compound of formula (VII)

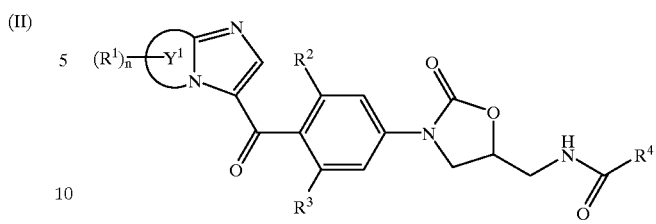
(VII)

c) reacting a compound of formula (II) with a compound of formula (VIII)

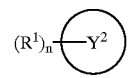
(VIII)

where $Y^2$ is a mono- or bicyclic- heteroaryl ring containing at least one nitrogen atom that is capable of quaternizing with (II), followed by reaction with a compound of formula (IX) or an acetylene of formula (IXa)

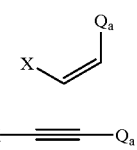
(IX)

(IXa)

where X is an electron withdrawing group within the definition of $R^1$ for formula (I) (such as cyano, nitro or $C_{1-4}$alkanoyl) and $Q_a$ is hydrogen or a group within the definition of $R^1$, to give a compound of formula (X)

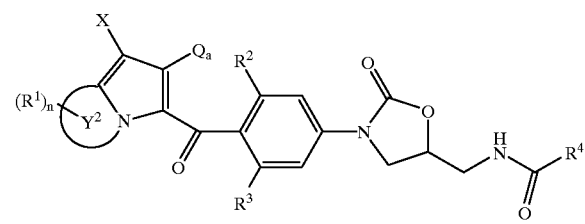
X d) reacting a compound of formula (XI)

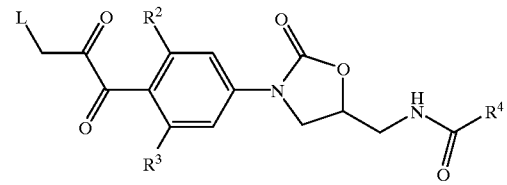
(XI)

where L is as defined above, with a compound of formula (VI) to give a compound of formula (XII)

(XII)

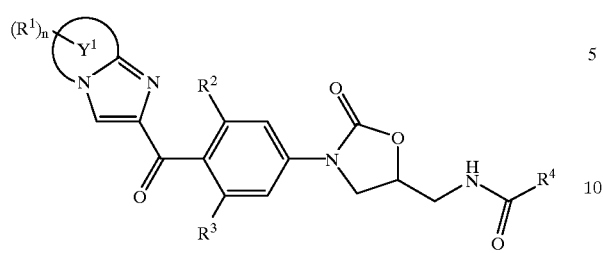

e) reacting a compound of formula (XIII)

(XIII)

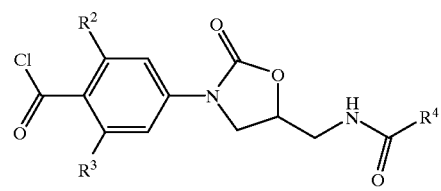

with a compound of formula (XIV)

(XIV)

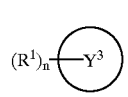

where $Y^3$ is a nitrogen-containing 5 membered heteroaryl ring or a nitrogen-containing 5 membered heteroaryl ring fused to a benzo ring which together form a bicyclic heteroaryl ring system without a bridgehead nitrogen, or $Y^3$ is a bicyclic or tricyclic heteroaryl ring system with at least one bridgehead nitrogen, and optionally with a further 1–3 heteroatoms chosen from oxygen, sulfur and nitrogen, to give a compound of formula (XV)

(XV)

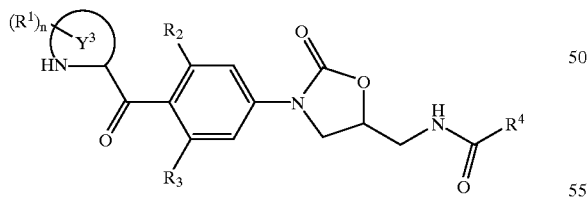

f) reacting a compound of formula (XVI)

(XVI)

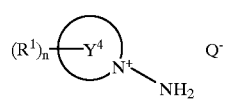

where $Y^4$ is a mono- or bicyclic-heteroaryl ring containing at least one nitrogen atom that is capable of forming a quaternary complex with the $NH_2$ group which is attached to this nitrogen and Q is a counter ion, with a compound of formula (XVII)

(XVII)

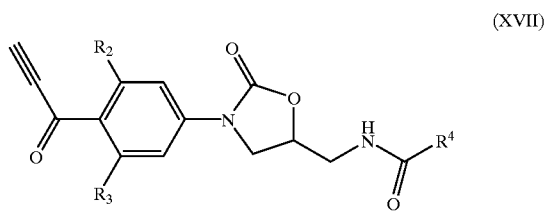

to give a compound of formula (XVIII)

(XVIII)

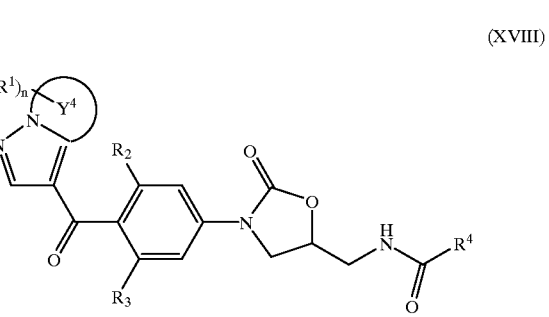

g) reacting a compound of formula (XIX)

XIX

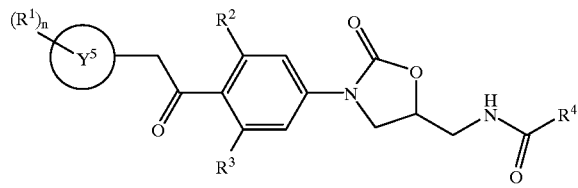

where $Y^5$ is a mono- or bicyclic-heteroaryl ring containing at least one nitrogen atom that is capable of quaternization, and the —$CH_2$—C(O)— linking group is ortho to this nitrogen in the heteroaryl ring, with p-toluenesulfonylazide to give a compound of formula (XX)

(XX)

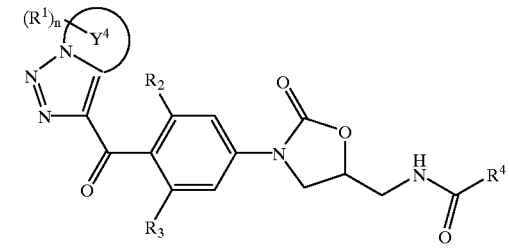

h) reacting a compound of formula (XI) with a compound of formula (XVI) to give a compound of formula (XXI)

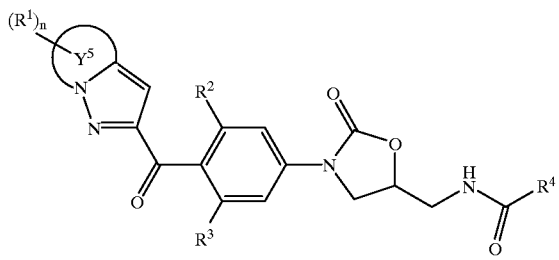

(XXI)

or i) For compounds of formula (I) in which A is thiazole or contains a thiazole moiety and is linked via the 2-position of said thiazole, by reaction of a compound of formula (II) with the parent thiazole compound; wherein:

L is a leaving group for example chloro, bromo, iodo, triflate or tosylate. Preferably L is bromo;

$Y^1$ is a mono- or bicyclic-heteroaryl ring containing at least one nitrogen atom that is capable of quaternizing. Where $Y^1$ contains more than one nitrogen atom preferably the molecule is symmetrical. Preferably $Y^1$ is pyridine, pyrimidine, pyridazine, pyrazine, thiazole, oxazole or N-substituted imidazole;

$Y^2$ is a mono- or bicyclic-heteroaryl ring containing at least one nitrogen atom that is capable of quaternizing. Preferably $Y^2$ is pyridine, pyrimidine, pyridazine, pyrazine, thiazole, oxazole or N-substituted imidazole;

$Y^3$ is a nitrogen-containing 5 membered heteroaryl ring or a nitrogen-containing 5 membered heteroaryl ring fused to a phenyl ring or $Y^3$ is a bicyclic or tricyclic heteroaryl ring system with at least one bridgehead nitrogen, and optionally with a further 1–3 heteroatoms chosen from oxygen, sulfur and nitrogen. Preferably $Y^3$ is pyrrole, imidazole, indole thiazole, oxazole or N-substituted imidazole;

$Y^4$ is a mono- or bicyclic-heteroaryl ring containing at least one nitrogen atom that is capable of quaternizing. Preferably $Y^4$ is pyridine, pyrimidine, pyridazine, pyrazine, thiazole, oxazole or N-substituted imidazole;

$Y^5$ is a mono- or bicyclic-heteroaryl ring containing at least one nitrogen atom that is capable of quaternizing. Preferably $Y^5$ is pyridine, pyrimidine, pyridazine, pyrazine, thiazole, oxazole or N-substituted imidazole;

Q is a counter ion. Preferably Q is chloro, bromo or iodo;

X is an electron withdrawing group. Preferably X is cyano;

$Q_a$ is hydrogen or a group within the definition of $R^1$. Preferably $Q_a$ is hydrogen; and thereafter if necessary i) forming a pharmaceutically acceptable salt,
ii) forming an in vivo hydrolysable ester or
iii) forming a suitable N-oxide.

The skilled reader will appreciate that not all nitrogen containing heteroaryl rings contain a nitrogen that is capable of quaternizing, for example the nitrogen in pyrrole cannot.

Specific reaction conditions for the above reactions are as follows:

a) Compounds of formula (II) and compounds of formula (III) are reacted together in the presence of an inert solvent (such as N,N-dimethylformamide, toluene or dioxan) at a temperature of 50–200° C., preferably 100–130° C. DMFDMA (IV) is then added and the mixture heated at a temperature of 50–200° C., preferably 150–180° C.

DMFDMA (IV) is commercially available and compounds of formula (III) are known, or are commercially available, or they may be prepared by standard manipulation of commercially available or known materials. Examples of these procedures for heterocyclic compounds are given in "The chemistry of heterocyclic compounds" published by Interscience and Houben-Weyl, Methoden der organischem chime, Heterarene III Teil 3, ed. E. Schaumann (1994).

N-(5S)-3-(4-[bromoacetyl]phenyl)-2-oxooxazolidin-5-ylmethylacetamide (XXII)

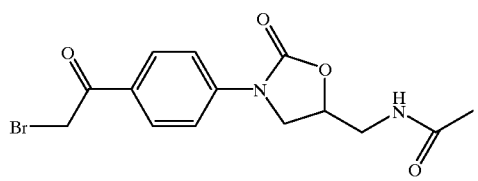

(XXII)

is a known compound (Britelli et. al., *J. Med. Chem.*, 1990, 33, 2569–2578).

N-(5S)-3-(4-[bromoacetyl]-3-fluorophenyl)-2-oxooxazolidin-5-ylmethylacetamide may be prepared by stirring N-(5S)-3-(4-acetyl-3-fluorophenyl)-2-oxooxazolidin-5-ylmethylacetamide (XXIII)

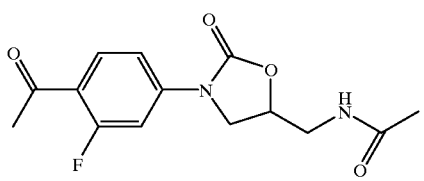

(XXIII)

with bromine in an organic acid (such as acetic acid) with a catalyst (such as methane sulfonic acid) at a temperature of 5–50° C., preferably 15–30° C. Compound (XXIII) is a known compound (*J. Med. Chem.*, 1992, 35(6), 1156–65).

N-(5S)-3-(4-[bromoacetyl]-3,5-difluorophenyl)-2-oxooxazolidin-5-ylmethylacetamide may be prepared by brominating N-(5S)-3-(4-acetyl-3,5-difluorophenyl)-2-oxooxazolidin-5-ylmethylacetamide (XXIV)

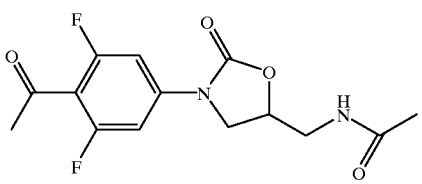

(XXIV)

with bromine in an organic acid (such as acetic acid) with a catalyst (such as methane sulfonic acid) at a temperature of 5–50° C., preferably 15–30° C.

N-(5S)-3-(4-acetyl-3,5-difluorophenyl)-2-oxooxazolidin-5-ylmethylacetamide may be prepared by reacting N-(5S)-3-(4-iodo-3,5-difluorophenyl)-2-oxooxazolidin-5-ylmethylacetamide (XXV)

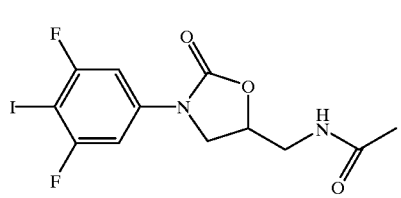

(XXV)

with butyl vinyl ether and a palladium catalyst under standard conditions (for example *J. Org. Chem.*, 1992, 5, 1481–1486). Compound (XXV) is a known compound (WO 94/13649 A1).

b) Compounds of formula (VI) are heated with DMFDMA (IV) in an inert solvent (such as toluene). The inert solvent is removed and the residue is redissolved in a polar solvent (such as N,N-dimethylformamide or dimethylacetamide or an alcohol (such as MeOH or EtOH)) with the compound of formula (II) and heated at 40–120° C., such as 60–120° C., preferably 80–100° C.

Compounds of formula (VI) are known, or are commercially available, or they may be prepared by standard manipulation of commercially available or known materials. Examples of these procedures for heterocyclic compounds are given in "The chemistry of heterocyclic compounds" published by Interscience and Houben-Weyl, Methoden der organischem chime, Heterarene III Teil 3, ed.

c) Compounds of formula (II) and compounds of formula (VIII) are heated together in the presence of an alcohol (such as EtOH) at 50–100° C., preferably at or near 80° C. The resulting compound is heated with a compound of formula (IX) with an oxidation catalyst (such as tetrapyridylcobalt dichromate; Xudong et al, *J. Chem. Soc.*, 1993, 2487), or with a compound of formula (IXa) in the absence of an oxidation catalyst, and a catalytic quantity of a weak base (such as pyridine) in an inert solvent (such as N,N-dimethylformamide) at a temperature of 70–110° C., preferably 80–100° C.

Compounds of formula (VIII), (IX) and (IXa) are known, or are commercially available, or they may be prepared by standard manipulation of commercially available or known materials. Examples of these procedures for heterocyclic compounds are given in "The chemistry of heterocyclic compounds" published by Interscience and Houben-Weyl, Methoden der organischem chime, Heterarene III Teil 3, ed. In process c) it will be appreciated that compounds of formula (IX) may be in cis- or trans- orientation.

d) Compounds of formula (XI) and compounds of formula (VI) are reacted together under standard conditions (for example *J. Het. Chem.*, 1989, 26, 293; *J. Med. Chem.*, 1988, 31(6), 1220–6) for example heating together in a solvent (such as N,N-dimethylformamide or THF/EtOH) at or near the boiling point of the solvent in the presence of a base (such as sodium carbonate or triethylamine).

Compounds of formula (XI) may be prepared, for example, by brominating compounds of formula (XXVI)

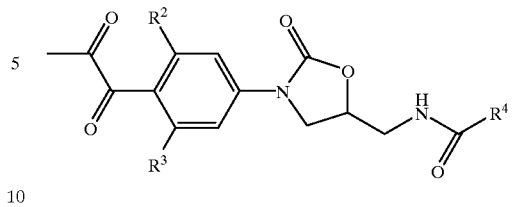

(XXVI)

under standard conditions (for example *Org. Synth.*, 1943, 480). Compounds of formula (XXVI) may be prepared by oxidising compounds of formula (XXVII)

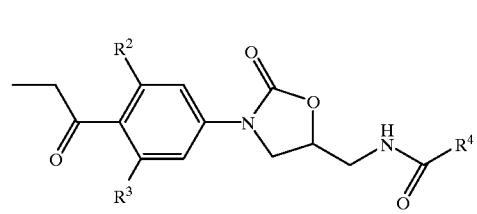

(XXVII)

under standard conditions (for example *Tet. Lett.*, 1977, 695). Compounds of formula (XXVII) may be prepared by acylating a compound of formula (XXVIII)

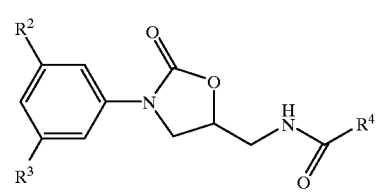

(XXVIII)

under standard Friedel Crafts conditions with propionic anhydride with methane sulfonic acid as the Lewis acid (for example *J. Med. Chem.*, 1989, 32, 1673). Compounds of formula (XXVIII) are known compounds (*J. Med. Chem.*, 1989, 32, 1673) or may be prepared by methods analogous to those disclosed in the reference.

e) Compounds of formula (XIII) and compounds of formula (XIV) are reacted together under standard conditions (for example: *Eur. J. Med. Chem.-Chim. Ther,.*, 1983, 18(4), 339–346).

Compounds of formula (XIII) may be prepared by chlorinating compounds of formula (XXIX)

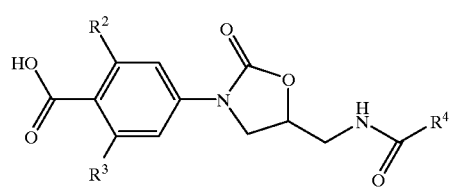

(XXIX)

under standard conditions. Compounds of formula (XXIX) may be prepared by the hydrolysis of the corresponding alkyl ester compounds known in the literature (for example *J. Med. Chem.*, 1990, 33, 2569–78) or they may be prepared by an analogous method to that disclosed in the reference. Compounds of formula (XIV) are known, or are commercially available, or they may be prepared by standard manipulation of commercially available or known materials. Examples of these procedures for heterocyclic compounds are given in "The chemistry of heterocyclic compounds" published by Interscience and Houben-Weyl, Methoden der organischem chime, Heterarene III Teil 3, ed.

Compounds of formula (XV) with a suitable $R^1$ substituent can optionally be further manipulated by processes known in the art to form further compounds of formula (I) where A is an F,P-ring system where F is a monocyclic or bicyclic heteroaryl ring and P is the pyrrole ring by suitable manipulation of the $R^1$ substituent. Thus, monocyclic pyrrole rings may, for example, be converted into bicyclic ring systems for example pyrrolothiazole.

f) Compounds of formula (XVI) and compounds of formula (XVII) are reacted together under standard conditions (for example: *J. Het. Chem.*, 1988, 25, 327).

Compounds of formula (XVII) may be prepared by oxidising compounds of formula (XXX)

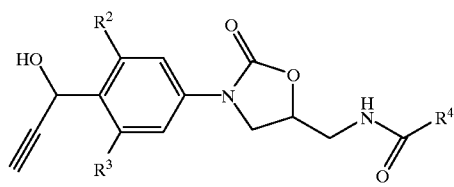

(XXX)

Compounds of formula (XXX) may be prepared by reacting compounds of formula (XXXI)

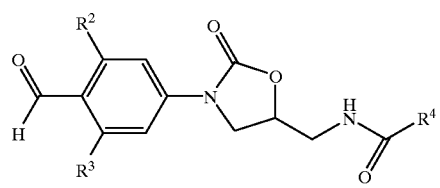

(XXXI)

with ethynylmagnesium bromide under standard Grignard conditions (for example *Synlett.*, 1993, 4, 281–2).

Compounds of formula (XXXI) are known in the literature (for example *J. Med. Chem.*, 1990, 33, 2569–78) or may be prepared by an analogous method to that disclosed in the reference. Compounds of formula (XVI) are known, or are commercially available, or they may be prepared by standard manipulation of commercially available or known materials (for example *Tet. Lett*, 1972, 4133).

g) Compounds of formula (XIX) and p-toluenesulfonylazide (*Synth Commun.*, 1987, 17, 1015) are reacted together under standard conditions (for example *Chem. Ber.*, 1966, 99, 2918).

Compounds of formula (XIX) may be prepared by reacting compounds (XXII), (XXIII) or (XXIV), or analogous compounds, with compounds of formula (XXXII)

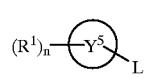

(XXXII)

where L is a leaving group as defined above and is ortho to the ring nitrogen that is capable of quaternization, under standard conditions (for example *Tet., Lett.*, 1994, 5185). Compounds of formula (XXII) are known, or are commercially available, or they may be prepared by standard manipulation of commercially available or known materials. Examples of these procedures for heterocyclic compounds are given in "The chemistry of heterocyclic compounds" published by Interscience and Houben-Weyl, Methoden der organischem chime, Heterarene III Teil 3, ed.

h) Compounds of formula (XI) and compounds of formula (XVI) are reacted together under standard conditions for example conditions similar to that disclosed in f).

i) Compounds of formula (II) and a parent thiazole compound as described in process i) are reacted in a solvent such as DMF, EtOH or MeOH at a temperature in the range ambient to 100° C. to give a quarternary compound; followed by treatment with at, or near, 2 mol.equivalents of aqueous sodium hydroxide (approximately 8%) in a solvent such as MeOH or EtOH (Ref. Singh et al, Ind.J.Chem., 31B, 217 (1992). DMFDMA is not necessary for this reaction.

The processes above were illustrated for the cases where L as defined in formula (II) and (XI) was bromine and $R^4$ as defined in formula (I) was methyl. It will be appreciated by the reader that in compounds where L and $R^4$ are other than these values the corresponding compounds can be prepared by conventional functional group modifications within the skill of the ordinary organic chemist. The processes a)–i) described above with other values for L and $R^4$ are a further feature of the invention. Furthermore. certain intermediate compounds described in the above processes are novel and are provided as a further feature of the invention.

The $R^4$ substituent may be introduced from compounds of formula (XXXIII)

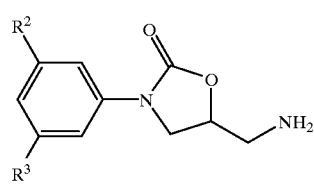

(XXXIII)

in the following manner:

i) When $R^4$ is $C_{1-4}$alkyl, the group —C(=O)$C_{1-4}$alkyl may be introduced into a compound of the formula (XXXIII) by standard acetylation procedures. For example, the amino group may be acetylated to give an acetamido group using the Schotten-Baumann procedure i.e. reacting the compound of the formula (XXXIII) with acetic anhydride in aqueous sodium hydroxide and THF in a temperature range of 0° C. to ambient temperature. Preferably the acylation is carried out in situ following the catalytic hydrogenation of a compound of the formula (XXXIV)

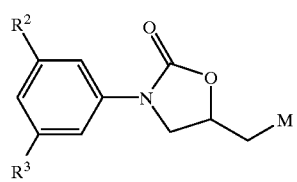

(XXXIV)

wherein M is azido, by performing the hydrogenation in the presence of acetic anhydride.

ii) When $R^4$ is hydrogen, the —CHO group may be introduced into the compound of the formula (XXXIII) by reacting the latter compound with formic acetic anhydride, in an inert organic solvent (such as THE), in a temperature range of 0° C. to ambient temperature, or by reacting it with ethyl formate in an inert organic solvent in the temperature range of 50–100° C.

iii) When $R^4$ is $C_{1-4}$alkoxy, the —$CO_2C_{1-4}$alkyl group may be introduced into the compound of the formula (XXXIII) by reacting the latter compound with $C_{1-4}$alkyl chloroformate, in the presence of an organic base (such as triethylamine), in an organic solvent such as dichloromethane and in a temperature range of 0° C. to ambient temperature.

iv) When $R^4$ is amino, the —$CONH_2$ group may be introduced into the compound of the formula (XXXIII) by reacting the latter compound either with potassium cyanate in aqueous acid (such as hydrochloric acid) in a temperature range of ambient temperature to 40° C. or with phenyl carbamate in glyme at reflux.

v) When $R^4$ is chloromethyl, dichloromethyl, cyanomethyl or methoxymethyl, the —$C(O)R^4$ group may be introduced into the compound of the formula (XXXIII) by reacting the latter compound with the appropriate acid chloride under standard conditions. The acid chloride may be prepared from the appropriate acid. When $R^4$ is acetylmethyl, the —$C(O)R^4$ group may be introduced into the amino compound by reacting the latter compound with diketene, in an inert organic solvent (such as THF), in a temperature range of 0° C. to ambient temperature. Alternatively, the compound of the formula (XXXIII) may be reacted with the appropriate acid anhydride, in dichloromethane or THF, in the presence of an organic base such as triethylamine and in a temperature range of 0° C. to ambient temperature, or the amino compound may be reacted with the appropriate acid in the presence of 1-(3-dimethylaminopropyl)-3-ethylcarbodiimide hydrochloride and an organic base (such as triethylamine), in an organic solvent (such as dichloromethane), in a temperature range of 0° C. to ambient temperature.

vi) When $R^4$ is methylamino, the —CONHMe group may be introduced into the compound of the formula (XXXIII) by reacting the latter compound with methyl isocyanate in an organic solvent (such as THF or acetonitrile), in a temperature range of 0° C. to ambient temperature.

vii) When $R^4$ is dimethylamino, the —$CONMe_2$ group may be introduced into the compound by of the formula (XXXIII) by reacting the latter compound with dimethylcarbamoyl chloride and triethylamine in an organic solvent (such as THF or acetonitrile), in a temperature range of 0° C. to ambient temperature.

Compounds of formula (XXXIII) may be prepared from compounds of formula (XXVIII) by cleavage of the acetamide with acid under standard conditions.

Compounds of formula XXXIII in which a suitable $R^4$ has been introduced may be subsequently modified to give the intermediates required by processes a)–i) using standard chemical modifications.

It will be appreciated by the reader that procedures for manipulation of $R^4$ as set out above can also be used on other compounds used or synthesised in procedures a)–i) with protection of functional groups where necessary, to make other compounds or formula (I).

Processes a)–i) describe the assembly of the ring A as the final as the final stage in the synthesis. It will be appreciated that the ring A may also be assembled at an earlier stage by reaction of a suitable heterocycle with, for example, 4-nitrobenzoyl chloride, followed by reduction of the nitro group to an amino group which can then be elaborated into a suitable 5-substituted oxazolidin-2-one ring using known chemistry (see for example, WO97/37980 and the references cited therein—the contents of which are hereby incorporated by reference).

It will be appreciated that certain of the various optional substituents $R^1$ in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; conversion of amino to alkanoylamino; oxidation of alkylthio to alkylsulfinyl or alkylsulfonyl; hydrogenation of halo to hydrogen.

Where ring A, as defined in formula (I), is a partially saturated ring system, it may be obtained by hydrogenation of the corresponding unsaturated ring system by techniques known in the art, for example catalytic hydrogenation in the presence of a transition metal catalyst or chemical hydrogenation for example with sodium and ammonia.

It will also be appreciated that in some of the reactions mentioned herein it may be necessary/desirable to protect any sensitive groups in the compounds (see, for example, Examples 47 and 49 where a protecting group is used to ensure reaction occurs at the desired centre). The instances where protection is necessary or desirable and suitable methods for protection are known to those skilled in the art. Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

For examples of protecting groups see one of the many texts on the subject, for example, "Protective Groups in Organic Synthesis" by Theodora Green (John Wiley & Sons). The protecting groups may be removed at any convenient stage in the synthesis using conventional techniques well known in the chemical art, such methods being chosen so as to effect removal of the protecting group with minimum disturbance of groups elsewhere in the molecule.

When a pharmaceutically-acceptable salt of a compound of the formula (I) is required, it may be obtained, for example, by reaction of said compound with the appropriate acid (which affords a physiologically acceptable anion), or with the appropriate base (which affords a physiologically acceptable cation), or by any other conventional salt formation procedure.

When an optically active form of a compound of the formula (I) is required, it may be obtained, for example, by carrying out one of the aforesaid procedures using an optically active starting material or by resolution of a racemic form of said compound using a conventional procedure.

According to a further feature of the invention there is provided a compound of the formula (I), or a pharmaceutically acceptable salt or an in vivo hydrolysable ester thereof, for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically acceptable salt, or an in vivo hydrolyzable ester thereof.

The invention also provides a compound of the formula (I), or a pharmaceutically acceptable salt, or an in vivo hydrolysable ester thereof for use as a medicament; and the use of a compound of the formula (I) of the present invention, or a pharmaceutically acceptable salt or an in vivo hydrolysable ester thereof, in the manufacture of a medicament for use in the production of an antibacterial effect in a warm blooded animal, such as man.

In order to use a compound of the formula (I) or a pharmaceutically acceptable salt or an in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or an in vivo hydrolysable ester thereof and a pharmaceutically acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

In addition to the compounds of the present invention the pharmaceutical composition of this invention may also contain or be co-administered with one or more known drugs selected from other clinically useful antibacterial agents (for example β-lactams or aminoglycosides). These may include penicillins, for example oxacillin or flucloxacillin and carbapenems, for example meropenem or imipenem, to broaden the therapeutic effectiveness. Compounds of this invention may also contain or be co-administered with bactericidal/permeability-increasing protein product (BPI) or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 100 mg and 1 g of the compound of this invention.

In another aspect a pharmaceutical composition of the invention is one suitable for intravenous, subcutaneous or intramuscular injection.

Each patient may receive, for example, a daily intravenous, subcutaneous or intramuscular dose of 5 mgkg$^{-1}$ to 20 mgkg$^{-1}$ of the compound of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I) or a pharmaceutically-acceptable salt thereof (hereafter compound X), for therapeutic or prophylactic use in humans:

| Tablet I | mg/tablet |
|---|---|
| Compound X. | 100 |
| Lactose Ph.Eur. | 179 |
| Croscarmellose sodium | 12.0 |
| Polyvinylpyrrolidone | 6 |
| Magnesium stearate | 3.0 |

(b)

| Tablet II | mg/tablet |
|---|---|
| Compound X | 50 |
| Lactose Ph.Eur. | 229 |
| Croscarmellose sodium | 12.0 |
| Polyvinylpyrrolidone | 6 |
| Magnesium stearate | 3.0 |

(c)

| Tablet III | mg/tablet |
|---|---|
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

| Capsule | mg/capsule |
|---|---|
| Compound X | 10 |
| Lactose Ph.Eur. | 389 |
| Croscarmellose sodium | 100 |
| Magnesium stearate | 1. |

| Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or EtOH or complexing agents such as hydroxy-propyl β cyclodextrin may be used to aid formulation.

Note

The above formulations may be obtained by conventional procedures well known in the pharmaceutical art. The tablets (a)–(c) may be enteric coated by conventional means, for example to provide a coating of cellulose acetate phthalate.

Antibacterial Activity

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of S. aureus and coagulase negative staphylococci. The antibacterial spectrum and potency of a particular compound may be determined in a standard test system.

The antibacterial properties of the compounds of the invention may also be demonstrated in-vivo in conventional tests.

The following results were obtained on a standard in-vitro test system. The activity is described in terms of the minimum inhibitory concentration (MIC) determined by the agar-dilution technique with an inoculum size of $10^4$ CFU/spot.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms.

When tested in the above in-vitro tests the compounds of this invention give MICs in the range 0.001–256 µg/ml.

The following data was obtained for Example 10

| ORGANISM | TYPE | MIC (µg/ml) |
|---|---|---|
| Staphylococcus aureus | Oxford | 0.13 |
| Staphylococcus aureus | Novb. Res. | 0.13 |
| Staphylococcus aureus | MRQR | 0.5 |
| Coagulase Negative Staphylococci | MS | 0.06 |
| Coagulase Negative Staphylococci | MR | 0.13 |
| Streptococcus pyogenes | C203 | 0.03 |
| Enterococcus faecalis | — | 0.25 |
| Bacillus subtilis | — | 0.125 |

Novb. Res. = Novobiocin resistant
MRQR = methicillin resistant quinoione resistant
MR = methicillin resistant
MS = methicillin sensitive.

EXAMPLES

The invention is now illustrated but not limited by the following Examples in which unless otherwise stated:

(i) evaporations were carried out by rotary evaporation in vacuo and work-up procedures were carried out after removal of residual solids by filtration;

(ii) operations were carried out at ambient temperature, that is typically in the range 18–26° C. and in air unless otherwise stated, or unless the skilled person would otherwise work under an inert atmosphere;

(iii) column chromatography (by the flash procedure) was performed on Merck Kieselgel silica (Art. 9385) unless otherwise stated;

(iv) yields are given for illustration only and are not necessarily the maximum attainable;

(v) the structure of end-products of the formula I were generally confirmed by NMR and mass spectral techniques. Proton magnetic resonance spectra were determined in deuterated dimethylsulfoxide unless otherwise stated using a Varian Gemini 2000 spectrometer operating at a field strength of 300 MHz (unless otherwise stated), or a Bruker AM250 spectrometer operating at a field strength of 250 MHz; chemical shifts are reported in parts per million downfield from tetramethysilane as an internal standard (δ scale) and peak multiplicities are shown thus: s, singlet. d, doublet; AB or dd, doublet of doublets; t, triplet, m, multiplet; mass spectrometry is performed by electrospray on a VG Platform;

(vi) intermediates were not generally fully characterised and purity was in general assessed by thin layer chromatographic, infra-red (IR), mass spectral (MS) or NMR analysis; and (vii) in which the following abbreviations may be used hereinbefore or hereinafter:

® is a Trademark;
DMF is N,N-dimethylformamide;
DMA is N,N-dimethylacetamide;

THF is tetrahydrofuran;
DMSO is dimethylsulfoxide;
CDCl$_3$ is deuterated chloroform;
MS is mass spectroscopy;
EtOH is ethanol;
MeOH is methanol;
EtOAc is ethyl acetate;
DMFDMA is dimethylformamide dimethylacetal;
1PS is (Whatman) phase-separating paper; and
mM is millimol (mmol)

Example 1

N-(](5S)-N-(4-[indolizin-3-ylcarbonyl]phenyl)-2-oxooxazolidin-5-yl]methyl)acetamide A mixture of 2-picoline (0.126 g, 1.35 mM) and N-(5S)-3-(4-[bromoacetyl]phenyl)-2-oxooxazolidin-5-ylmethylacetamide (Britelli et. al.,*J. Med. Chem.*, 1990, 33, 2569–2578; 0.48 g, 1.35 mM) in DMF (5 ml) was heated at 150° C. for 30 minutes and allowed to cool. DMFDMA (0.24 g, 1.2 mM) was added and the mixture heated at 160° C. for 20 minutes. More (0.2 g) DMFDMA was added and heating continued for a further hour. The mixture was evaporated and the residue was purified by dry column chromatography on silicagel (Merck, Art.7736), eluting first with dichloromethane and then, increasing amounts of MeOH up to 5% to give the title compound (28 mg). Mp 209–210° C.; MS 378 (MH$^+$); NMR: 1.83 (3H, s), 3.29 (nH+H$_2$O), 3.45 (2H, t), 3.83 (1H, m), 4.20 (1H, t), 4.78 (1H, m), 6.68–7.83 (9H, aromatic), 8.23 (1H, t), 9.82 (1H, d); C$_{21}$H$_{19}$N$_3$O$_4$ requires C, 66.8; H, 5.1; N, 11.1%: found C, 66.9; H, 4.7; N, 10.8%.

Example 2

N-([(5S)-N-(4-[6-methylindolizin-3-ylcarbonyl]phenyl)-2-oxooxazolidin-5-yl]methyl)acetamide A mixture of 2,5-dimethylpyridine (0.13 g, 1.2 mM) and N-(5S)-3-(4-[bromoacetyl]phenyl)-2-oxooxazolidin-5-ylmethylacetamide (0.355 g, 1 mM) in DMF (2 ml) was heated at 120° C. for 80 minutes and allowed to cool. DMFDMA (0.2 g, 1.6 mM) was added and the mixture heated at 170° C. for 10 minutes. The mixture was cooled and water (~20 ml) added and the mixture was extracted with EtOAc (3×). The combined extracts were filtered (Whatman 1PS paper) and evaporated. The residue was purified by flash column chromatography on silicagel, eluting with 10% MeOH in dichloromethane and recrystallization from acetonitrile to give the title compound (51 mg). Mp 237–239° C.; MS 393 (MH$^-$); NMR 1.82 (3H, s), 2.33(3H, s), 3.43 (2H, t), 3.8 (1H, t), 4.17 (1H, t), 4.75 (1H, m), 6.6(1H, d), 7.2(1H,d), 7.3(1H, d), 7.68(2H, d), 7.8(2H, d), 8.25(1H, t), 9.67 (1H, s); C$_{22}$H$_{21}$N$_3$O$_4$ 0.3 H$_2$O requires C, 66.6 H, 5.5; N, 10.6%: found: C, 66.7; H, 5.1; N, 10.8%.

Example 3

N-([(5S)-N-(4-[6-cyanoindolizin-3-ylcarbonyl]phenyl)-2-oxooxazolidin-5-yl]methyl)acetamide In a similar manner to Example 2 but starting from 2-cyano-6-methylpyridine, was prepared the title compound in 2% yield as a solid recrystallized from MeOH. MS 403 (MH$^+$); NMR 1.82 (3H, s), 3.44 (2H, m), 3.82 (1H, t), 4.2 (1H, t), 4.76 (1H, m), 6.87(1H, t), 7.48(1H,d), 7.5(1H, d), 7.6(2H, d), 7.83–7.98(3H, d+m), 8.25(1H, t), 10.17 (1H, s).

Example 4

N-([(5S)-N-(4-[3-methylpyrrolo[1,2-a]pyrazin-6-ylcarbonyl]phenyl)-2-oxooxazolidin-5-yl]methyl)acetamide In a similar manner to Example 2 but starting from 2,5-dimethylpyrazine was prepared the title compound in 5% yield as a solid. Mp 248–250° C.; MS 393 (MH$^+$); NMR 1.8 (3H, s), 2.47(3H+H$_2$O), 3.42(2H, t), 3.8 (1H, t), 4.2 (1H, t), 4.78 (1H, m), 6.98(1H, d), 7.4(1H, d), 7.7(1H, d), 7.87(2H, d), 8.26(1H, t), 9.1(1H, s), 9.23(1H, s): C$_{21}$H$_{20}$N$_4$O$_4$. 0.5 H$_2$O requires C, 62.8; H, 5.3; N, 14.%: found: C, 63.2; H, 4.9; N; 13.9%.

Example 5

N-([(5S)-N-(4-[imidazo[1,2-a]pyridin-3-ylcarbonyl]phenyl)-2-oxooxazolidin-5-yl]methyl)acetamide A mixture of 2-aminopyridine (0.94 g, 10 mM) and DMFDMA (1.31 g, 11 mM) in toluene (5 ml) was heated at reflux for 2 hours. Solvent was evaporated and a portion of the residue (0.22 g, 1.5 mM) dissolved in DMF (2 ml). N-(5S)-3-(4-[bromoacetyl]phenyl)-2-oxooxazolidin-5-ylmethylacetamide (0.355 g, 1mM) was added and the mixture heated at 80° C. for 1 hour. Water (~20 ml) was added to the solution and the precipitated solid was isolated by centrifugation and washed by centrifugation with water, acetone (2×) and ether to give the title product as a solid (0.156 g). Mp 218–220° C.; MS 379 (MH$^+$); NMR 1.86 (3H, s), 3.45 (2H, m), 3.85 (1H, m), 4.23 (1H, t), 4.8 (1H, m), 7.32 (1H, t), 7.65–7.83 (3H, c), 7.86–8 (3H, c), 8.25 (1H, t), 8.29 (1H, s), 9.65 (1H, d); C$_{20}$H$_{18}$N$_4$. O$_4$ 0.6 H$_2$O requires C, 61.7; H, 5.0; N, 14.4%: found: C, 61.4; H, 4.5; N, 14.1%.

Example 6

N-([(5S)-N-(4-[imidazo[1,2-a]pyrimidin-3-ylcarbonyl]phenyl)-2-oxooxazolidin-5-yl]methyl)acetamide In a similar manner to Example 5 but starting from 2-aminopyrimidine was prepared the title compound in 45% yield as a solid. Mp 257–260° C.; MS 380 (MH$^-$); NMR 1.88 (3H, s), 3.32(nH+H$_2$O), 3.49 (2H, t), 3.88 (1H, m), 4.26 (1H, t), 4.83 (1H, m), 7.49 (1H, m), 7.9 & 8.02 (4H, AB), 8.27 (1H, t), 8.48 (1H, s), 8.91 (1H, m), 9.90 (1H, m); C$_{19}$H$_{17}$N$_5$O$_4$. . 0.25 H$_2$O requires C, 59.4; H, 4.6; N, 18.2%: found: C, 59.4; H, 4.4; N, 17.9%.

Example 7

N-([(5S)-N-(4-[5,7-dimethylimidazo[1,2-a]pyrimidin-3-ylcarbonyl]phenyl)-2-oxooxazolidin-5-yl]methyl)acetamide In a similar manner to Example 5 but starting from 2-amino-4,6-dimethylpyrimidine was prepared the title compound in 15% yield (after flash column chromatography on silicagel, eluting with 10% MeOH in dichloromethane and trituration with acetone) as a solid. Mp 253–254° C.; MS 408 (MH$^+$); NMR (250 MHz)1.81 (3H, s), 2.6(3H, s), 2.63(3H, s) 3.45 (2H, t), 3.83(1H, m), 4.2(1H, t), 4.77(1H, t), 7.19(1H, s), 7.75 (2H, d), 8.02(2H, d), 8.08(1H, s), 8.22 (1H, t); C$_{21}$H$_{21}$N$_5$O$_4$. 0.33 H$_2$O requires C, 61.1; H, 5.3; N, 16.9%: found: C, 61.2; H,5.2; N, 16.5%.

The following Examples 8–11, 13–25 and 27–29 were made in a similar manner to Example 5, starting from the appropriate 2-amino heteroaryl. When a solid was obtained on addition of water, it was purified by centrifugal washing with MeOH and diethyl ether. Where the crude product was an oil or was water-soluble, it was extracted exhaustively into EtOAc and purified by flash column chromatography on silicagel, eluting with 5% MeOH in dichloromethane.

Example 8

N-([(5S)-N-(4-[6-bromoimidazo[1,2-a]pyridin-3-ylcarbonyl]phenyl)-2-oxooxazolidin-5-yl]methyl) acetamide The title product was obtained as a solid in 29% yield. Mp 230–232° C.; MS 459 (MH$^+$); NMR (250 MHz) 1.83 (3H, s), 3.4 (2H, m), 3.83(1H, m), 4.2(1H, t), 4.8 (1H, m), 7.77 (2H, d), 7.8 (2H, c), 7.96 (2H, d), 8.23 (1H, t), 8.3 (1H, s), 9.75 (1H, d); $C_{20}H_{17}BrN_4O_4$. 0.5 $H_2O$ requires C, 51.5; H, 3.9; N, 12%: found: C, 51.6; H, 3.7; N, 11.9%.

Example 9

N-([(5S)-N-(4-[imidazo[2,1-a]isoquinol-3-ylcarbonyl]phenyl)-2-oxooxazolidin-5-yl]methyl) acetamide The title product was obtained as a solid in 18% yield. Mp 239–240° C.; MS 429 (MH$^+$); NMR 1.8 (3H, s), 3.4 (2H, m), 3.83(1H, m), 4.1(1H, t), 4.76 (1H, m), 7.6 (1H, d), 7.8 (3H, m), 8 (3H, m), 8.2 (2H, m), 8.62 (1H, d), 9.23 (1H, d); $C_{24}H_{20}N_4O_4$. 0.3 $H_2O$ requires C, 66.4, H, 4.8; N, 12.9%: found: C, 66.5; H, 4.6; N, 12.9%.

Example 10

N-([(5S)-N-(4[imidazo[2,1-b]thiazol-5-ylcarbonyl]phenyl)-2-oxooxazolidin-5-yl]methyl)acetamide The title product was obtained as a solid in 1% yield. MS 385 (MH$^+$); NMR 1.66 (3H, s), 3.25 (2H+$H_2O$), 3.66(1H, m), 4.05(1H, t), 4.6 (1H, m), 7.45 (1H, d), 7.6 (2H, d), 7.79(2H, d), 7.92(1H, s), 8.1 (1H, m), 8.3 (1H, d).

Example 11

N-([(5S)-N-(4-[6,8-dichloroimidazo[1,2-a]pyridin-3-ylcarbonyl]phenyl)-2-oxooxazolidin-5-yl]methyl) acetamide The title product was obtained as a solid in 14% yield. Mp 228–229° C.; MS 447, 449 (MH); NMR 1.8 (3H, s), 3.44 (2H, m), 3.83(1H, m), 4.1(1H, t), 4.78 (1H, m), 7.72 (2H, d), 7.96 (2H, d), 8.1 (1H, s), 8.2 (1H, t), 8.37 (1H, s), 9.6 (1H, d); $C_{20}H_{16}Cl_2N_4O_4$ 0.6 $H_2O$ requires C, 52.4; H, 3.8; N, 12.2%: found: C, 52.4; H, 3.6; N, 11.6%.

Example 12

N-([(5S)-N-(4-[1-cyanoindolizin-3-ylcarbonyl]phenyl)-2oxooxazolidin-5-yl]methyl)acetamide A mixture of pyridine (0.08 g, 1 mM) and N-(5S)-3-(4-[bromoacetyl]phenyl)-2-oxooxazolidin-5-ylmethylacetamide (0.355 g. 1 mM) in EtOH (5 ml) was heated at 80° C. for 2 hours. The solid which had appeared was filtered and washed with EtOH to give the pyridinium quaternary salt (0.211 g) which, with acrylonitrile (0.103 g, 0.32 mM) and tetrapyridylcobalt dichromate (Xudong et al, *J. Chem. Soc.,* 1993, 2487; 0.2 g, 0.32 mM) in DMF (5 ml) and pyridine (0.1 ml), was heated at 90° C. under argon for 2.25 hours. The mixture was evaporated and the residue purified by flash column chromatography on silicagel, eluting with 10% MeOH in dichloromethane to give a solid which was washed with MeOH and ether to give the title product (0.112 g). Mp 255–257° C.; MS 403 (MH$^+$); NMR 1.81 (3H, s), 3.45 (2H, m), 3.83 (1H, m), 4.2 (1H, t), 4.7 (1H, m), 7.32 (1H, t), 7.63 (1H, t), 7.72 (2H, d), 7.88 (2H, d), 8.2 (1H, t), 9.77 (1H, d); $C_{22}H_{18}N_4O_4$ 0.3 $H_2O$ requires C, 64.8; H, 4.6; N, 13.7%: found: C, 64.9; H, 4.4, N, 13.8%.

Example 13

N-([(5S)-N-(4-[7-methylimidazo[1,2-a]pyridin-3-ylcarbonyl]phenyl)-2-oxooxazolidin-5-yl]methyl) acetamide The title product was obtained as a solid in 44% yield. Mp 254–256° C.; MS 393 (MH$^+$); NMR 1.8 (3H, s), 2.42(3H, s), 3.45 (2H, t), 3.82 (1H, t), 4.2 (1H, t), 4.76 (1H, m), 7.18(1H,d), 7.66(1H, s), 7.73(2H, d), 7.92 (2H, d), 8.2 (1H, s), 8.24(1H, t), 9.47 (1H, d); $C_{21}H_{20}N_4O_4$ 0.3 $H_2O$ requires C, 63.4 H; 5.2; N, 14.1%: found: C, 63.5; H, 4.8; N, 14%.

Example 14

N-([(5S)-N-(4-[6-chloroimidazo[1,2-a]pyridin-3-ylcarbonyl]phenyl)-2-oxooxazolidin-5-yl]methyl) acetamide The title product was obtained as a solid in 14% yield. Mp 234–235° C.; MS 413,415 (MH$^+$); NMR 1.8 (3H, s), 3.45 (2H, t), 3.84(1H, m), 4.2(1H, t), 4.76 (1H, m), 7.8 (2H, m), 7.95 (2H+1H, t), 8.23 (1H, t), 8.32 (1H, s), 9.65 (1H, s); $C_{20}H_{17}ClN_4O_4$ 0.4 $H_2O$ requires C, 57.4; H, 4.2; N, 13.4%: found: C, 57.2; H, 3.9; N, 13.3%.

Example 15

N-([(5S)-N-(4-[6-nitroimidazo[1,2-a]pyridin-3-ylcarbonyl]phenyl)-2-oxooxazolidin-5-yl]methyl) acetamide The title product was obtained as a solid in 37% yield. Mp 223–225° C.; NMR 1.8 (3H, s), 3.45 (2H, t), 3.83(1H, m), 4.2(1H, t), 4.76 (1H, m), 7.76 (2H, d), 8.03 (2H+1H, m). 8.24 (1H, t), 8.3 (1H, d), 8.52 (1H, s); $C_{20}H_{17}N_5O_6$ 0.3 $H_2O$ requires C, 56; H, 4.1; N, 16.3%: found: C, 56.2; H, 3.8; N, 16.1%.

Example 16

N-([(5S)-N-(4-[8-nitroimidazo[1,2-a]pyridin-3-ylcarbonyl]phenyl)-2-oxooxazolidin-5-yl]methyl) acetamide The title product was obtained as a solid in 11% yield. Mp 229–230° C.; MS 424 (MH$^+$); NMR 1.8 (3H, s), 3.45 (2H, t), 3.84(1H, m), 4.2(1H, t) 4.76 (1H, m), 4.74 (1H, t), 7.76 (2H, d), 8 (2H, d), 8.25 (1H, t), 8.4 (1H, s), 8.58 (1H, d), 9.82 (1H, d); $C_{20}H_{17}N_5O_6$ 0.8 $H_2O$ requires C, 54.9; H, 4.3; N, 16%: found: C, 55.2; H, 3.9; N, 15.4%.

Example 17

N-([(5S)-N-(4-[5,7-dimethylimidazo[1,2-a]pyridin-3-ylcarbonyl]phenyl)-2-oxooxazolidin-5-yl]methyl) acetamide The title product was obtained as a solid in 5% yield. MS 407 (MH$^+$); NMR 1.81 (3H, s), 2.43(3H, s), 2.52(3H, s), 3.42 (2H, t), 3.81(1H, m), 4.2(1H, t), 4.76 (1H, m), 7(1H, s), 7.51 (1H, s), 7.75 (2H, d), 7.93(1H, s), 8.05 (2H, d), 8.25 (1H, t); $C_{22}H_{22}N_4O_4$ 1.6 $H_2O$ requires C, 60.7; H, 5.8; N, 12.9%: found: C, 60.3; H, 5.3; N, 12.5%.

Example 18

N-([(5S)-N-(4-[5-methylimidazo[1,2-a]pyridin-3-ylcarbonyl]phenyl)-2-oxooxazolidin-5-yl]methyl)acetamide The title product was obtained as a solid in 1% yield. MS 393 (MH$^+$); NMR (250 MHz) 1.73 (3H, s), 2.56(3H, s), 3.46 (2H, t), 3.85(1H, m), 4.23(1H, t), 4.78 (1H,m), 7.13(1H, d), 7.63(11H, m), 7.75 (2H+1H, m), 8.05 (2H, d), 8.1(1H, s), 8.23 (1H, t).

Example 19

N-([(5S)-N-(4-[8-bromo-6-methylimidazo[1,2-a]pyridin-3-ylcarbonyl]phenyl)2-oxooxazolidin-5-yl]methyl)acetamide The title product was obtained as a solid in 31% yield. Mp 221–223° C.; MS 471.5, 473.5 (MH$^+$): NMR (250 MHz) 1.8 (3H, s), 2.33 (3H, s) 3.4 (2H, m), 3.8(1H, t), 4.16(1H, t), 4.75 (1H, m), 7.7(2H, d), 7.9 (2H+1H, m), 8.2 (2H, m), 9.37 (1H, s); $C_{21}H_{19}BrN_4O_4$ requires C, 52.9; H, 4.1; N, 11.7%: found: C, 53; H, 4; N, 11.6%.

Example 20

N-([(5S)-N-(4-[8-benzyloxyimidazo[1,2-a]pyridin-3-ylcarbonyl]phenyl)-2-oxooxazolidin-5-yl]methyl)acetamide The title product was obtained as a solid in 58% yield. Mp 193–195° C. MS 485 (MH$^+$); NMR (250 MHz) 1.8(3H, s), 3.43 (2H, m), 3.8(1H, m), 4.2(1H, t), 4.75 (1H, m), 5.35(2, s), 7.18(2H, m), 7.37(3H, m), 7.5(2H, d), 7.72 (2H, d), 7.93 (2H, d), 8.14 (1H, s), 8.25 (1H, t), 9.17 (1H, m); $C_{27}H_{24}N_4O_4$ 0.3 $H_2O$ requires C, 66.2; H, 5.1; N, 11.4%: found C, 66.1; H, 4.9; N, 11.3%.

Example 21

N-([(5S)-N-(4-[6-trifluoromethylimidazo[1,2-a]pyridin-3-ylcarbonyl]phenyl)-2-oxooxazolidin-5-yl]methylacetamide The title product was obtained as a solid in 40% yield. Mp 243–245° C.; MS 447 (MH$^+$); NMR 1.82 (3H, s), 3.4 (2H, m), 3.82(1H, m), 4.2(1H, t), 4.76 (1H, m), 7.76 (2H, d), 7.95 (2H+1H, m), 8.1 (1H, d), 8.21 (1H, t), 8.45 (1H, s), 9.95(1H, m); $C_{21}H_{17}F_3N_4O_4$ 1.3 $H_2O$ requires C, 55.8; H, 3.9; N, 12.4%: found: C, 55.6; H, 3.6; N, 12.1%.

Example 22

N-([(5S)-N-(4[imidazo[1,2-a]pyridin-3-ylcarbonyl]{3-fluorophenyl})-2-oxooxazolidin-5-yl]methyl)acetamide In a similar manner to Example 5 but starting from N-(5S)-3-(4-[bromoacetyl]-3-fluorophenyl)-2-oxooxazolidin-5-ylmethylacetamide, was prepared the title product as a solid in 15% yield, mp 196–198° C.; MS 397 (MH$^+$); NMR 1.85 (3H, s), 3.46 (2H, m), 3.85 (1H, m), 4.2 (1H, t), 4.8 (1H, m), 7.39 (1H, t), 7.65–7.84 (3H, c), 7.8 (1H, d), 8.13 (1H, s), 8.22 (1H, t), 9.65 (1H, d); $C_{20}H_{17}FN_4O_4$ requires C, 60.4; H, 4.1; N, 13.9%: found: C, 60.6; H, 4.3; N, 14.1%.

The N-(5S)-3-(4-[bromoacetyl]3-fluorophenyl)-2-oxooxazolidin-5-ylmethylacetamide was prepared as follows Bromine (0.18 ml) was added to a stirred solution of N-(5S)-3-(4-acetyl-3-fluorophenyl)-2-oxooxazolidin-5-ylmethylacetamide (*J. Med. Chem.*, 1992, 35(6), 1156–65.) (1 g, 3.4 mM) in acetic acid (9 ml) and methanesulfonic acid (0.77 ml). Stirring was continued for 3 hours and the solution was poured into water (50 ml) The solid which separated after trituration was filtered and dried to give 0.82 g of a mixture of monobromo- and dibromoketones which was used without purification; MS; 374, 454 (MH$^+$).

Example 23

N-([(5S)-N-(4-[8-methoxycarbonylimidazo[1,2-a]pyridin-3-ylcarbonyl]phenyl)-2-oxooxazolidin-5-yl]methyl)acetamide The title product was obtained as a solid in 18% yield. Mp 202–204° C.; MS: 437 (MH$^+$); NMR: 1.85 (3H, s), 3.28 (nH+H$_2$O), 3.43 (2H, t), 3.85 (1H, m), 3.92 (3H, s) 4.20 (1H, t), 4.75 (1H, m), 7.41 (1H, t), 7.74 (2H, d), 7.94 (2H, d), 8.21 (2H, t+s), 8.31 (1H, s), 7.99 (1H, d); $C_{22}H_{20}N_4O_6$ 0.1H$_2$O requires C, 58.15; H, 4.88; N, 12.3%: found: C, 57.8; H, 4.6; N, 11.8%

Example 24

N-([(5S)-N-(4-[6-methoxycarbonylimidazo[1,2-a]pyridin-3-ylcarbonyl]phenyl)-2-oxooxazolidin-5-yl]methyl)acetamide The title product was obtained as a solid in 47% yield. Mp 231–233° C.; MS: 437 (MH$^+$); NMR: 1.81 (3H, s), 3.28 (nH+H$_2$O), 3.45 (2H, t), 3.83 (1H, m), 3.92 (3H, s), 4.20 (1H, t), 4.78 (1H, m), 7.78 (2H, d), 7.9–8.05 (4H, aromatics), 8.22 (1H, t), 8.39 (1H, s) $C_{22}H_{20}N_4O_6$. 1.5 H$_2$O requires C, 57.02; H, 5.0; N, 12.09%: found: C, 57.3; H, 4.7; N, 12.1%.

Example 25

N-([(5S)-N-(4-[7-phenylimidazo[1,2-a]pyridin-3-ylcarbonyl]phenyl)-2-oxooxazolidin-5-yl]methyl)acetamide The title product was obtained as a solid in 47% yield. Mp 256–258° C.; MS: 455 (MH$^+$); MNR: 1.83 (3H, s), 3.28 (nH+H$_2$O), 3.43 (2H, t), 3.82 (1H, m), 4.20 (1H, t), 4.78 (1H, m), 7.42–7.58 (3H, m's), 7.7–7.8 (3H, m's), 7.9–8.0 (4H, m's), 8.19 (1H, s), 8.23 (1H, t), 8.30 (1H, t). 9.62 (1H, d); $C_{26}H_{22}N_4O_4$ .0.25H$_2$O requires C, 68.04; H, 4.94; N, 12.2%: found: C, 68.1; H, 4.8; N, 12.4%.

Example 26

N-([(5S)-N-(4-[8-hydroxyimidazo[1,2-a]pyridin-3-ylcarbonyl]phenyl)-2-oxooxazolidin-5-yl]methyl)acetamide The title compound of Example 20 (0.12 g, 0.248 mM) in MeOH (40 ml) was treated with 10% palladium on carbon (0.06 g) and the mixture stirred under an atmosphere of hydrogen for 4.5 hours. Catalyst was removed by filtration and the filtrate evaporated. The solid residue was purified by chromatography on a Mega Bond Elut® silica column, eluting first with dichloromethane and then with 4% MeOH-dichloromethane to give a solid which was triturated with ether containing a little MeOH to give the title compound as a solid. Mp 253–255° C. (decomp.). MS: 395 (MH+); NMR: 1.86(3H, s), 3.46(2H, t), 3.85(1H, m), 4.24(1H, t), 4.80(1H, m), 6.95(1H, d), 7.14(1H, t) 7.75(2H, d, aromatic), 7.95(2H, d, aromatic), 8.18(1H, s). 8.25(1H, t), 9.16(1H, d), 10.8(1H, brs).

Example 27

N-([(5S)-N-(4-[6-fluoroimidazo[1,2-a]pyridin-3-ylcarbonyl]phenyl)-2-oxooxazolidin-5-yl]methyl) acetamide The title product was obtained as a solid in 32% yield. Mp 224–226° C.; MS 397 (MH+); NMR 1.8 (3H, s), 3.42 (2H, t), 3.8(1H, m), 4.2(1H, t), 4.76 (1H, m), 7.68–7.83 (2H+1H, m), 7.95 (2H+1H, m), 8.2 (1H, t), 8.3 (1H, d), 8.32 (1H, s), 9.6 (1H, m); $C_{20}H_{17}N_4O_4F.0.7\ H_2O$ requires C, 58.7; H, 4.5; N, 13.7%: found: C, 58.5; H, 4.2; N, 13.6%.

The 2-amino-5-fluoropyridine starting material was obtained as described in Hand et al, Synth, 1989, 905.

Example 28

N-([(5S)-N-(4-[6-cyanoimidazo[1,2-a]pyridin-3-ylcarbonyl]phenyl)-2-oxooxazolidin-5-yl]methyl) acetamide The title product was obtained as a solid in 32% yield. Mp 224–226° C.; MS 397 (MH+); NMR 1.8 (3H, s), 3.43 (2H, t), 3.82(1H, m), 4.2 (1H, t), 4.77 (1H, m), 7.75 (2H, d), 7.9–8.04 (4H, m), 8.23 (1H, t), 8.42 (1H, s), 10.02 (1H, brm); $C_{20}H_{17}N_4O_4F.0.7\ H_2O$ requires C, 58.7; H, 4.5; N, 13.7%: found: C, 58.5; H, 4.2; N, 13.6%.

Example 29

N-([(5S)-N-(4-[1-methylimidazo[1,2-a]imidazol-5-ylcarbonyl]phenyl)-2-oxooxazolidin-5-yl]methyl]) acetamide The title product was obtained as a solid in 5% yield; MS 382 (MH+); NMR 1.8 (3H, s), 3.42 (2H, t), 3.72 (3H, s), 3.8(1H, m), 4.18 (1H, t), 4.72 (1H, m), 7.39 (1H, s) 7.68 (2H+1H, m). 7.83 (1H, s), 7.93 (2H, d), 8.23 (1H, t); $C_{19}H_{19}N_5O_4.0.3\ H_2O$ requires C, 59; H, 5.1; N, 18.1%: found: C, 59; H, 4.9; N, 17.7%.

Example 30

N-([(5S)-N-(4-[2,3-dihydroimidazo[2.1-b]thiazol-5-ylcarbonyl]phenyl)-2-oxooxazolidin-5-yl]methyl) acetamide The method described for Example 5 was followed with the second-stage reaction mixture on heating at 100° C. giving a polar product. The solvent was evaporated, the residue treated with EtOH (5 ml) and sodium bicarbonate (0.32 g, 3 mM) and the mixture heated at 100° C. for 4 hours. The mixture was filtered and the filtrate evaporated. The residue was purified by column chromatography, eluting with 7% MeOH in dichloromethane to give a solid which was triturated with acetone and filtered off to give the title compound as a solid in 8% yield. Mp 259–260° C.; MS 387 (MH+); NMR 1.8 (3H, s), 3.4 (2H, t), 3.8(1H, m), 4 (2H, t), 4.16 (1H, t), 4.5 (2H, t), 4.75 (1H, m), 7.6 (1H, s), 7.7 (2H, d) 7.88 (2H, d), 8.22 (1H, t); $C_{18}H_{18}N_4O_4S$. requires C, 55.9; H, 4.7; N, 14.5%: found: C, 55.8; H, 5.1; N, 15.3%.

Example 31

N-([(5S)-N-(4-[6-{dimethylaminomethyleneaminocarbonyl}imidazo[1,2-a]pyridin-3-ylcarbonyl]phenyl)-2-oxooxazolidin-5-yl]methyl)acetamide The title product was obtained as a solid in 39% yield using an analogous procedure to that in Example 5, with 2-(dimethylaminomethyleneamino)-5-(dimethylaminomethyleneaminocarbonyl)pyridine as starting material; MS 477 (MH+); NMR 1.82 (3H, s), 3.2 (3H, s), 3.22 (3H, s), 3.45 (2H, t) 3.82(1H, m), 4.2 (1H, t), 4.78 (1H, m), 7.71 (2H, d), 7.88 (2H, d), 7.95 (2H), 8.22 (1H+1H, m), 8.31 (1H, s), 8.7 (1H, s) 10.42 (1H, brs); $C_{23}H_{28}N_6O_5.0.1\ H_2O$ requires C, 58.7H, 6; N, 17.9%: found: C, 59.2; H, 5.2; N, 17.9%. The 2-(dimethylaminomethyleneamino)-5-(dimethylaminomethyleneaminocarbonyl)pyridine used as starting material was obtained from the reaction of 2-amino-5-carbamoylpyridine and DMFDMA in toluene at 130° C.

Example 32

N-([(5S)-N-(4-[thiazol-2-ylcarbonyl]phenyl)-2-oxooxazolidin-5-yl]methyl)acetamide Using an analogous method to that of of Singh et al., Ind. J. Chem., 31B 217 (1992), a mixture of thiazole (0.085 g, 1 mM) and N-(5S)-3-(4-[bromoacetyl]phenyl)-2-oxooxazolidin-5-ylmethylacetamide (0.355 g, 1 mM) in DMF (2 ml) was stirred and heated at 100° C. for 6 hours. Solvent was evaporated and the residue triturated with acetone and filtered to give the quaternary salt (0.348 g) which was stirred in MeOH (10 ml) and treated with 8% aqueous sodium hydroxide (0.8 ml, 1.58 mM). After 20 hours the solution was diluted with water (20 ml) and extracted three times with EtOAc. The combined extracts were filtered (1PS paper) and evaporated. The residue was purified by flash-column chromatography, eluting with 5% MeOH/dichloromethane to give the title product as a solid (0.031 g). MS 346 (MH+); NMR 1.8 (3H, s), 3.4 (2H, m), 3.8(1H, t), 4.17(1H, t), 4.75 (1H, m), 7.73 (1H, d), 8.2 (2H+H, m), 8.48 (2H, d).

Example 33

N-[(5S)-N-(4[benzothiazol-2-ylcarbonyl]phenyl)-2-oxooxazolidin-5-yl]methyl)acetamide The method described for Example 32 was followed but starting from benzothiazole to give the title compound as a solid in 6% yield. Mp 213–215° C.; MS 396 (MH+); NMR 1.8 (3H, s), 3.4 (2H, t), 3.82(1H, m), 4.2 (1H, t), 4.77 (1H, m), 7.63 (2H, m), 7.78 (2H, d), 8.23 (1H, m), 8.5 (2H, d); $C_{20}H_{17}N_3O_4S.\ 0.2\ H_2O$ requires C, 60.2; H, 4.4; N, 10.5%: found: C, 60.2; H, 4; N, 10.4%.

Example 34

N-([(5S)-N-(4-[6-aminoimidazo[1,2a]pyridin-3-ylcarbonyl]phenyl)-2-oxooxazolidin-5-yl]methyl) acetamide A mixture of the title compound of Example 15 (1.75 g. 4.14 mM) and 10% palladium on charcoal containing 50% water (0.37 g.) in acetic acid (20 ml) was hydrogenated at ambient temperature and atmospheric pressure until hydrogen uptake was complete. The catalyst was removed by filtration and the filtrate evaporated. The residue was purified by flash-column chromatography, eluting with 15% MeOH/dichloromethane to give the title product as a solid (0.4 g). Mp 245–248° C.); MS 394 (MH+); NMR 1.82 (3H, s), 3.42 (2H, t), 3.81(1H, t), 4.18 (1H, t), 4.76 (1H, m), 5.4 (2H, s), 7.2 (1H, dd), 7.6 (2H, d), 7.68 (2H, d), 7.87 (2H, d), 8.21 (1H, t), 9.08 (1H, d).

Example 35

N-([(5S)-N-(4-[6-acetamidoimidazo[1,2-a]pyridin-3-ylcarbonyl]phenyl)-2-oxooxazolidin-5-yl]methyl) acetamide The method used to make Example 34 was repeated, and the solution of the hydrogenated product in acetic acid was evaporated. The residue was azeotroped with toluene to give, after trituration with ether, a solid which was purified by column chromatography by gradient elution increasing in polarity from dichloromethane to 10% MeOH/dichloromethane to give the title product in 11% yield. MS: 436 (MH+); NMR:1.83 (3H, s); 2.1 (3H, s) 3.44 (2H, t); 3.83 (1H, m); 4.2 (1H, t); 4.76 (1H, m); 7.7 (3H, m); 7.83 (1H, d); 7.9 (2H, d); 8.19 (1H,s); 8.24 (1H, t); 10.3 (2H, br.s.)

Example 36

N-([(5S)-N-(4-[6-(hydroxyacetamido)imidazo[1,2-a]pyridin-3-ylcarbonyl]phenyl)-2oxooxazolidin-5-yl]methyl)acetamide The title product from Example 34 (0.142 g. 0.36 mM) was stirred in 50% aqueous acetone (8 ml). Sodium bicarbonate (0.302 g. 3.6 mM) was added, followed by acetoxyacetyl chloride (0.19 ml.1.77 mM) and the mixture stirred for 18 hours. The solid was filtered and washed with water, MeOH and ether to give N-([(5S)-N-(4-[6-(acetoxyacetamido)imidazo[1,2-a]pyridin-3-ylcarbonyl]phenyl)-2-oxooxazolidin-5-yl]methyl)acetamide (0.1 g) MS: 494 (MH+). This material (0.09 g. 0.183 mM) was stirred in suspension for 20 hours in a saturated solution of ammonia in MeOH (4 ml). The solid was filtered and washed with MeOH and ether to give the title product (0.066 g). MS: 452 (MH+); NMR (250 MHz) 2.03 (3H, s); 3.64 (2H, t); 4.03 (1H, m); 4.26 (2H, d); 4.4 (1H, t); 4.97 (1H, m); 5.93 (1H, t); 7.93 (2H, d); 8.04 (2H, m); 8.13 (2H, d); 8.42 (1H+1H, s+t); 10.32 (1H, s); 10.61 (1H, s).

Example 37

N-([(5S)-N-(4-[6-methylthioimidazo[1,2-a]pyridin-3-ylcarbonyl]phenyl)-2-oxooxazolidin-5-yl]methyl)acetamide Using an analogous method and work up to that used in Examples 8–11, 13–25 and 27–29, the title product was obtained as a solid in 11% yield. MS: 425 (MH+); NMR 1.83 (3H, s); 2.59 (3H, s); 3.44 (2H, t); 3.83 (1H, m); 4.2 (1H, t); 4.76 (1H, m); 7.68 (1H, m), 7.73 (2H, d); 7.3 (1H, d); 7.93 (2H, d); 8.24 (2H, m); 9.45 (1H, s).

Example 38

N-([(5S)-N-(4-[6-(methylsulfinyl)imidazo[1,2-a]pyridin-3-ylcarbonyl]phenyl)-2-oxooxazolidin-5-yl]methyl)acetamide A solution of sodium periodate (0.067 g. 0.313 mM) in water (2.5 ml) was added to a stirred suspension of the title product from Example 37 (0.12 g. 0.283 mM) in MeOH (10 ml) and the mixture heated at gentle reflux for 3 hours. The mixture was filtered hot and allowed to cool. The solid which precipitated was filtered, washed with water and ether and purified by chromatography on a BondElut silica column with gradient elution increasing in polarity from dichloromethane to 10% MeOH/dichloromethane to give the title compound (0.07 g). MS: 441 (MH+); NMR 1.83 (3H, s); 2.9 (3H, s); 3.45 (2H, t); 3.83 (1H, m); 4.2 (1H, t); 4.75 (1H, m); 7.75 (2H, d) 7.9 (1H, m); 7.96 (2H; d); 8.05 (1H, d); 8.24 (1H, t); 8.36 (1H, s); 9.83 (1H, s).

Example 39

N-([(5S)-N-(4-[6-(methylsulfonyl)imidazo[1,2-a]pyridin-3-ylcarbonyl]phenyl)-2-oxooxazolidin-5-yl]methyl)acetamide A solution of Oxone (0.356 g. 0.579 mM) in water (2.5 ml) was added to a stirred suspension of the title product from Example 37 (0.117 g. 0.276 mM) in EtOH (10 ml) and the mixture heated at gentle reflux for 2.75 hours. The mixture was allowed to cool. The solid which precipitated was filtered, washed with water and ether to give the title compound (0.1 09 g). MS: 457 (MH+); NMR(250 MHz) 1.83 (3H, s); 3.38 (3H, s); 3.45 (2H, t); 3.85 (1H, m); 4.23 (1H, t); 4.79 (1H, m); 7.78 (2H, d); 8.0 (2H, d); 8.08 (2H, m); 8.24 (1H, t); 8.48 (1H, s); 10.01 (1H, s).

Example 40

N-([(5S)-N-(4-[6-(2-hydroxyethylthio)imidazo[1,2-a]pyridin-3-ylcarbonyl]phenyl)-2-oxooxazolidin-5-yl]methyl)acetamide Using an analogous method and work up to that used in Examples 8–11, 13–25 and 27–29, the title product was obtained as a solid in 8.5% yield. MS: 455 (MH+); NMR 1.83 (3H, s); 3.07 (2H, t); 3.43 (2H, t); 3.6 (2H, m); 3.81 (1H, m); 4.2 (1H, t); 4.76 (1H, m); 4.96 (1H, t); 7.73 (3H, m); 7.84 (1H, d); 7.96 (2H, d); 8.25 (2H, m); 9.6 (1H, s).

The starting material, 2-amino-5-[(2-hydroxyethyl)thio]pyridine was made as follows:

A mixture of 2-amino-5-iodopyridine (Bull. Chem. Soc. Japan, 61 1683 (1988); 0.886 g. 4.03 mM), sodium methoxide (0.435 g. 8.05 mM), cuprous chloride (0.08 g. 0.81 mM), 2-mercaptoethanol (0.15 ml. 2.14 mM) and DMF (30 ml) was heated under argon at 120° C. for 2 hours. The mixture was cooled, poured into water and basified with aqueous potassium carbonate. The mixture was extracted three times with EtOAc. The combined extracts were filtered, washed with water, dried (MgSO$_4$) and evaporated. The residue was purified by chromatography on a BondElut column in dichloromethane, with gradient elution increasing in polarity from dichloromethane to 3% MeOH/dichloromethane to give the title starting material as a solid (0.194 g.) MS: 171 (MH+).

Example 41

N-([(5S)-N-(4-[6-(2,3-dihydroxypropythio)imidazo[1,2-a]pyridin-3-ylcarbonyl]phenyl)-2-oxooxazolidin-5-yl]methyl)acetamide Using an analogous method and work up to that used in Examples 8–11, 13–25 and 27–29, the title product was obtained as a solid in 0.4% yield MS: 485 (MH+); NMR 1.82 (3H, s); 2.94 (1H, m); 3.16 (1H, m); 3.42 (4H, m); 3.62 (1H, m); 3.82 (1H, m); 4.2 (1H,t); 4.63 (1H, t); 4.76 (1H, m); 5.0 (1H, d); 7.73 (3H, m); 7.84 (1H, d); 7.95 (2H, d); 8.25 (2H, m); 9.6 (1H, s). The starting material, 2-amino-5-[(2,3-dihydroxypropyl)thio]pyridine was made was made as an oil containing DMF (1.46 g.) using the method described in Example 40 for the preparation of starting material, but starting from 3-mercapto-1,2-propanediol. MS: 201 (MH+).

Example 42

N-([(5S)-N-(4-[6-hydroxymethylimidazo[1,2-a]pyridin-3-ylcarbonyl]phenyl)-2-oxooxazolidin-5-yl]methyl)acetamide Using an analogous method and work up to that used in Examples 8–11, 13–25 and 27–29, the title product was obtained from 2-amino-5-hydroxymethylpyridine (Balkovec, J. Antibiot. 44, 1172 (1991)), in 3% yield. MS: 409 (MH+); NMR(250 MHz) 1.83 (3H, s); 3.45 (2H, t); 3.85 (1H, m); 4.21 (1H, t); 4.65 (2H, d); 4.8 (1H, m); 5.5 (1H, t); 7.62 (1H, m); 7.75 (2H, d); 7.83 (1H, d); 7.95 (2H, d); 8.23 (2H, t); 9.6 (1H, s).

Example 43

N-([(5S)-N-(4-[6-bromoimidazo[1,2-a]pyrazin-3-ylcarbonyl]phenyl)-2-oxooxazolidin-5-yl]methyl)acetamide Using an analogous method and work up to that used in Examples 8–11, 13–25 and 27–29, the title product was obtained as a solid in 18% yield. Mp 216–220° C.: MS 458 (MH$^+$); NMR 1.82 (3H, s), 3.4 (2H, t), 3.82(1H, t), 4.2(1H, t), 4.77 (1H, m), 7.76 (2H, d), 8.0 (2H, d), 8.2 (1H, t), 8.5 (1H, s), 9.25(1H, s); 9.54 (1H, s).

Example 44

N-([(5S)-N-(4-[6-chloroimidazo[1,2-b]pyridazin-3-ylcarbonyl]phenyl)-2-oxooxazolidin-5-yl]methyl)acetamide Using an analogous method and work up to that used in Examples 8–11, 13–25 and 27–29, the title product was obtained as a solid in 13% yield. Mp 194–196° C.; MS 414 (MH$^+$); NMR 1.82 (3H, s); 3.41 (2H, t); 3.82(1H, t); 4.19(1H, t); 4.79(1H, m); 7.64(1H, d); 7.72 (2H, d); 7.95 (2H, d); 8.22 (1H, t); 8.29 (1H, s), 8.4(1H, d).

Example 45

N-([(5S)-N-(4-[imidazo[1,2-a]pyrazin-3-ylcarbonyl]phenyl)-2-oxooxazolidin-5-yl]methyl)acetamide Using an analogous method and work up to that used in Examples 8–11, 13–25 and 27–29, the title product was obtained as a solid in 11% yield. Mp 254–256° C.; MS 380 (MH$^+$); NMR 1.8 (3H, s); 3.44 (2H, 0t); 3.82(1H, t); 4.2(1H, t); 4.76(1H, m); 7.76 (2H, d); 8.0 (2H, d); 8.22 (1H, t); 8.25 (1H, d), 8.45(1H, s); 9.36 (1H, s); 9.41 (1H, d)

Example 46

N-([(5S)-N-(4-[6-chloroimidazo[1,2-a]pyrimidin-3-ylcarbonyl]phenyl)-2-oxooxazolidin-5-yl]methyl)acetamide Using an analogous method and work up to that used in Examples 8–11, 13–25 and 27–29, the title product was obtained as a solid in 62% yield. MS: 414.5 (MH$^+$); NMR 1.83 (3H, s); 3.45 (2H, t); 3.83 (1H, m); 4.2 (1H, t); 4.77 (1H, m); 7.76 (2H, d); 7.99 (2H, d); 8.24 (1H, t); 8.48 (1H, s); 8.92 (1H, s); 9.88 (1H, s).

Example 47

N-([(5S)-N-(4-[pyrrol-2-ylcarbonyl]phenyl)-2-oxooxazolidin-5-yl]methyl)acetamide A solution of N-([(5S)-N-(4-[1-(2-trimethylsilylethoxymethyl)pyrrol-2-ylcarbonyl]phenyl)-2-oxooxazolidin-5-yl]methyl)acetamide (0.79 g, 1.72 mM) in dry THF (15 ml) was stirred under nitrogen and treated dropwise with a solution of tetrabutylammonium fluoride in THF (1 M, 8.6 mM). The solution was stirred for 2.5 hours and then heated at reflux for 4 hours. The solution was evaporated and the residue partitioned between EtOAc and water. The organic layer was washed with water, dried (Mg SO$_4$) and evaporated. The residue was purified by column chromatography, eluting with a gradient increasing in polarity from 2% to 10% MeOH/dichloromethane to give the title product as a solid (0.16 g). Mp 202–205° C., MS: 328 (MH$^+$). NMR: 1.97 (3H, s); 3.42 (nH+H$_2$O); 3.58 (2H, t); 3.94 (1H, m); 4.32 (1H, t); 4.89 (1H, m); 6.40 (1H, m); 6.93 (1H, m); 7.32 (1H, m); 7.82 (2H, d); 8.01 (2H, d); 8.37 (1H, t); 12.10 (1H, s).

The starting material for Example 47 was made as described below:

A solution of 2-(4-nitrobenzoyl) pyrrole (White et al., J. Org. Chem., 42 4284 [1977]; 2 g. 9.26 mM) in DMF (5 ml) was added dropwise to a stirred suspension of sodium hydride (0.42 g of a 60% dispersion in mineral oil, 1.05 mM) in DMF (15 ml). After 10 minutes, the mixture was cooled to 5° C. and 2-trimethylsilylethoxymethyl chloride (1.7 ml) was added dropwise and the mixture stirred for 10 minutes. The cooling bath was removed and stirring continued for 1.5 hours. The mixture was poured into aqueous sodium carbonate solution and extracted into EtOAc. The organic layer was washed with water, dried (MgSO$_4$) and evaporated. The residue was purified by column chromatography in dichloromethane, eluting with a gradient increasing in polarity from 2% to 5% MeOH/dichloromethane to give 2-(4-nitrobenzoyl)-1-(2-trimethylsilylethoxymethyl)pyrrole as an oil (2.3 g). MS: 347 (MH$^+$) NMR: −0.1 (9H, s); 0.82 (2H, t) 3.5 (2H, t); 5.71(2H, s); 6.28 (1H, m); 6.84 (1H, m); 7.52 (1H, m), 7.92 (2H, d); 8.36 (2H, d).

Iron powder (0.52 g) was added in three portions to a stirred solution of 2-(4-nitrobenzoyl)-1-(2-trimethylsilylethoxymethyl)pyrrole (0.59 g. 1.7 mM) in acetic acid at 65° C. Heating was continued for 2 hours and solvent was evaporated and the residue partitioned between EtOAc and water. The organic layer was washed with water, dried (Mg SO$_4$) and evaporated, to give 2-(4-aminobenzoyl)-1-(2-trimethylsilylethoxymethyl)pyrrole as an oil (0.5 g). MS: 317 (MH$^+$). NMR: −0.18 (9H, s); 0.74 (2H, t) 3.38 (2H, t); 5.64 (2H, s); 5.95 (2H, s); 6.16 (1H, m); 6.59 (2H, d) 6.6 (1H, m); 7.3 (1H, m); 7.57 (2H, d).

Ethyl chloroformate (0.21 g, 1.95 mM) was added dropwise to a stirred solution of 2-(4-aminobenzoyl)-1-(2-trimethylsilylethoxymethyl)pyrrole (0.5 g. 1.58 mM) in pyridine (5 ml) at 5° C. After 5 minutes the cooling bath was removed and stirring continued for 1.75 hours. The mixture was treated with MeOH (2 ml) and evaporated and the residue partitioned between EtOAc and aqueous sodium bicarbonate solution. The organic layer was washed with water, aqueous citric acid, dried (MgSO$_4$) and evaporated. to give 2-(4-ethoxycarbonylaminobenzoyl)-1-(2-trimethylsilylethoxymethyl)pyrrole as an oil (0.58 g). MS: 389 (MH$^+$). NMR: 0.0 (9H, s); 0.89 (2H, t); 1.38 (3H, t) 3.57 (2H, t); 4.28 (2H, q); 5.8 (2H, s); 6.34 (1H, m); 6.82 (1H, m); 7.50 (1H, m); 7.7 (2H, d); 7.83 (2H, d); 10.1 (1H, br s).

n-Butyl lithium (4.6 ml. of 1.6 M solution in THF, 7.36 mM) was added to a stirred solution of t-butanol (0.505 g) in dry THF at −20° C. under nitrogen and the mixture stirred for 20 minutes. The temperature was lowered to −60° C. and 2-(4-ethoxycarbonylaminobenzoyl)-1-(2-trimethylsilylethoxymethyl)pyrrole (2.2 g. 5.67 mM) added over 15 minutes. The mixture was stirred for 50 minutes and a solution of R-(−) glycidyl butyrate (0.9 g. 6.25 mM) in dry THF (5 ml) added. The mixture was allowed to warm to ambient temperature and stirred for 24 hours. MeOH (20 ml) was added and the solution evaporated and the residue partitioned between EtOAc and water The organic layer was washed with water, dried (MgSO$_4$) and evaporated. The residue was purified by column chromatography using 2% MeOH/dichloromethane as eluant, to give 5(R)-hydroxymethyl-N-(4-[1-(2-trimethylsilylethoxymethyl)pyrrol-2-ylcarbonyl]phenyl)oxazolidin-2-one as an oil (0.77 g; MS: 417 (MM$^-$)).

This product was reacted in dichloromethane solution (15 ml) containing triethylamine (0.33 g) with methanesulfonyl chloride added dropwise (0.18 ml) at 5° C. Stirring was continued at ambient temperature for 1 hour to give, after washing the solution with water, drying (MgSO$_4$) and evaporating, 5(R)-methylsulfonyloxymethyl-N-(4-[1-(2-trimethylsilylethoxymethyl)pyrrol-2-ylcarbonyl]phenyl) oxazolidin-2-one (0.95 g; MS: 495 (MH$^+$)).

This material (1.92 mM) in DMF (5 ml) was treated with sodium azide (0.26 g. 0.4 mM) with stirring. The mixture was heated at 75° C. for 3 hours, cooled and partitioned between EtOAc and water. The organic layer was washed with water, dried (Mg SO$_4$) and evaporated to give 5(R)-azidomethyl-N-(4-[1-(2-trimethylsilylethoxymethyl)pyrrol-2-ylcarbonyl]phenyl)oxazolidin-2-one as an oil (0.92 g; MS: 442 (MH$^+$)).

The azide (0.192 mM—based on 100% yield from from preceding reaction) in EtOAc (25 ml) and acetic anhydride (0.18 ml. 0.192 mM) was hydrogenated for 2.5 hours in the presence of 10% palladium on charcoal containing 50% water (0.29 g). The mixture was filtered and the filtrate stirred with 5% aqueous sodium bicarbonate solution (30 ml), washed with water, dried (Mg SO$_4$) and evaporated to give N-([(5S)-N-(4-[1-(2-trimethylsilylethoxymethyl) pyrrol-2-ylcarbonyl]phenyl)-2-oxooxazolidin-5-yl]methyl) acetamide (0.95 g) as an oil. MS: 458 (MH$^+$); NMR:(250 MHz) –0.11(9H, s); 0.98(2H, t); 1.83 (3H, s); 3.4–3.52 (4H, m); 3.81 (1H, m); 4.19 (1H, t); 4.76 (1H, m); 5.71(2H, s); 6.24 (1H, m); 6.71 (1H, m); 7.43 (1H, m); 7.68 (2H, d); 7.8 (2H, d); 8.23 (1H, t).

Example 48

N-([(5S)-N-(4-[1-methylpyrrol-2-yl carbonyl] phenyl)-2-oxooxazolidin-5-yl]methyl)acetamide The title compound of Example 47 (0.14 g, 0.43 mM) in DMF (1.4 ml) was stirred under nitrogen and cooled to 5° C. Sodium hydride (0.019 g of a 60% dispersion in mineral oil, 0.47 mM) was added and the mixture stirred for 15 minutes. Iodomethane (30 µl) was added, the mixture stirred for 10 minutes at 5° C. and at ambient temperature for 2 hours. The mixture was evaporated and the residue partitioned between EtOAc and water. The organic layer was washed with water dried (MgSO$_4$) and evaporated. The residue was purified by column chromatography in dichloromethane, eluting with a gradient increasing in polarity from 2% to 10% MeOH/ dichloromethane to give the title product as an oil (0.13 g). MS: 342 (MH$^+$); NMR: 1.83 (3H, s); 3.28 (nH+H$_2$O); 3.42 (2H, t); 3.80 (1H, m); 3.92 (3H, s); 4.9 (1H, t); 4.75 (1H, m); 6.16 (1H, m); 6.64 (1H, m); 7.23 (1H, m); 7.67 (2H, d); 7.80 (2H, d); 8.22 (1H, t).

Example 49

N-([(5S)-N-(4-[imidazol-2-ylcarbonyl]phenyl)-2-oxooxazolidin-5-yl]methyl)acetamide Starting from N-([(5S)-N-(4-[1-(2-trimethylsilylethoxymethyl)imidazol-2-ylcarbonyl]phenyl)-2-oxooxazolidin-5-yl]methyl)acetamide, the title compound was made, by an analogous method to that of Example 47 as a solid in 53% yield. MS: 329 (MH$^+$); NMR (250 MHz) 1.84 (3H, s); 3.47 (2H, t); 3.83 (1H, m); 4.21 (1H, t); 4.77 (1H, m); 7.23 (1H, s); 7.47 (1H, s); 7.71 (2H, d); 8.22 (1H, t); 8.6 (2H, d); 13.35 (1H, s).

The necessary starting material was made by an analogous procedure to that described for the preparation of the starting material in Example 47 but starting from 2-(4-nitrobenzoyl) imidazole (Synthesis, 675 (1978)).

Example 50

N-([(5S)-N-(4-[1-methylimidazol-2-ylcarbonyl] phenyl)-2-oxooxazolidin-5-yl]methyl)acetamide Using the title product of Example 49 as starting material and employing an analogous method to that of Example 48, the title product was obtained in 31% yield as a solid. MS: 343(MH$^+$); NMR 1.83 (3H, s); 3.45 (2H, t); 3.83 (1H, m); 4.0 (3H, s); 4.18 (1H, t); 4.78 (1H, m); 7.2 (1H, s); 7.53 (1H, s); 7.69 (2H, d); 8.12 (1H, t); 8.35 (2H, d).

What is claimed is:
1. A compound of formula (I),

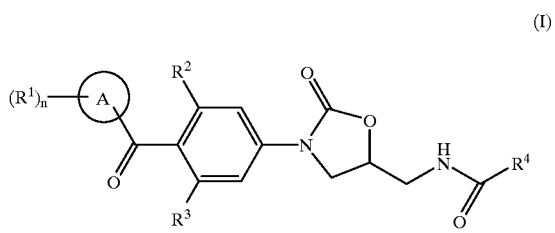

wherein:

A is a bicyclic benzo system containing a 5-membered heteroaryl ring, wherein the heteroaryl ring contains 1 nitrogen atom and optionally 1–3 further heteroatoms selected from oxygen, sulfur and nitrogen and is linked via a ring carbon atom in the 5-membered heteroaryl ring; or A is a bicyclic or tricyclic heteroaryl ring system with at least one bridgehead nitrogen and optionally a further 1–3 heteroatoms chosen from oxygen, sulfur and nitrogen and is linked via a ring carbon atom in a ring containing a bridgehead nitrogen;

$R^1$ is attached to a ring carbon atom and is hydroxy, halo, amino, nitro, cyano, carboxy, thiol, $C_{1-4}$alkanoyloxy, $C_{1-4}$alkoxycarbonyl, dimethylaminomethyleneaminocarbonyl, $C_{1-4}$alkyl, $C_{2-4}$alkenyl, $C_{2-4}$alkynyl, $C_{1-4}$alkoxy, $R^5$—, $R^5$—O—, $R^5$—$C_{1-4}$alkyl-, $R^5$—$C_{1-4}$alkoxy- or $R^5$—C(O)NH—; or $R^1$ is attached to a ring nitrogen atom where such substitution does not result in quaternization and is selected from $R^7$—, $R^7$—C(O)— or $C_{1-4}$alkoxyC (O)—;

$R^2$ and $R^3$ are independently hydrogen or fluoro;

$R^4$ is hydrogen, $C_{1-4}$alkyl, $C_{1-4}$alkoxy, amino, chloromethyl, dichloromethyl, cyanomethyl, methoxymethyl, acetylmethyl, methylamino and dimethylamino;

$R^5$ is optionally substituted phenyl, an optionally substituted 5- or 6-membered heteroaryl ring, an optionally substituted 5- or 6-membered heterocycle or an optionally substituted bicyclic heteroaryl ring, hydroxyC$_{1-4}$alkyl, carbamoyl, N—(C$_{1-4}$alkyl)carbamoyl, N,N—(C$_{1-4}$alkyl)$_2$carbamoyl, thiocarbamoyl, N—(C$_{1-4}$alkyl) thiocarbamoyl, N,N—(C$_{1-4}$alkyl)$_2$thiocarbamoyl, trifluoromethyl, C$_{1-4}$alkanoylamino, wherein the C$_{1-4}$alkanoyl group is optionally substituted by hydroxy, $R^6$-thio, $R^6$-sulfinyl, or $R^6$-sulfonyl; wherein optional substituents for $R^5$ include all of the values of $R^1$ except those where $R^1$ includes an $R^5$ group;

$R^6$ is C$_{1-4}$alkyl optionally substituted by one or more groups independently selected from cyano, hydroxy and C$_{1-4}$alkoxy, C$_{1-4}$alkanoyl, sulfonamido, C$_{1-4}$alkylamino, di(C$_{1-4}$alkyl)amino, C$_{1-4}$alkoxyC$_{1-4}$alkyl, carbamoylC$_{1-4}$alkyl or cyanoamino;

R$^7$ is C$_{1-4}$alkyl optionally substituted by cyano, hydroxy or C$_{1-4}$alkoxy; and n is 0–6;

or a pharmaceutically acceptable salt; or for a compound of the formula (I) containing a carboxy or hydroxy group, an in vivo hydrolysable ester thereof, wherein esters for carboxy are selected from C$_{1-6}$alkoxymethyl esters, C$_{1-6}$alkanoyloxymethyl esters, phthalidyl esters, C$_{3-8}$cycloalkoxycarbonyloxyC$_{1-6}$alkyl esters, 1,3-dioxolen-2-onylmethyl esters and C$_{1-6}$alkoxycarbonyloxyethyl esters; and wherein esters for hydroxy are selected from phosphate esters, α-acyloxyalkyl ethers, alkanoyl, benzoyl, phenylacetyl, substituted benzoyl, alkoxycarbonyl, dialkylcarbamoyl, N-(dialkylaminoethyl)-N-alkylcarbamoyl, dialkylminoacetyl and carboxyacetyl, wherein substituted benzoyl is benzoyl substituted by morpholino or piperazino linked from a ring nitrogen atom via a methylene group to the 3- or 4- position of the benzoyl ring.

2. A compound according to claim 1, wherein:

A is a 5,5- or 5,6- fused ring system with at least one bridgehead nitrogen;

R$^1$ is halo, amino, (1–4C)alkyl, (1–4C)alkanoylamino that is optionally substituted by hydroxy, cyano, nitro, trifluoromethyl, benzyloxy, (1–4C)alkoxycarbonyl, phenyl, hydroxy, dimethylaminomethyleneaminocarbonyl; (1–4C)alkylthio that is optionally substituted by one or two hydroxy groups, (1–4C)alkylsulfinyl, (1–4C)alkylsulfonyl or hydroxy-(1–4C)alkyl;

n is 0–2; and

R$^4$ is C$_{1-4}$alkyl.

3. A compound according to claim 1, wherein

A is a 5,5- or 5,6- fused ring system with at least one bridgehead nitrogen;

R$^1$ is halo;

n is 0 or 1; and

R$^4$ is C$_{1-4}$alkyl.

4. A compound according to claim 2, wherein

A is a 5,5- or 5,6- fused ring system with at least one bridgehead nitrogen;

R$^1$ is halo;

n is 0 or 1; and

R$^4$ is C$_{1-4}$alkyl.

5. A compound according to claim 1, wherein A is imidazo[1,2-a]pyridine, imidazo[1,5-a]pyridine, imidazo[1,2-c]pyrimidine, imidazo[1,2-a]pyrimidine, imidazo[1,5-a]pyrimidine, imidazo[5,1-b]thiazole, imidazo[2,1-b]thiazole, imidazo[5,1-b]oxazole or imidazo[2,1-b]oxazole.

6. A compound according to claim 2, wherein A is imidazo[1,2-a]pyridine, imidazo[1,5-a]pyridine, imidazo[1,2-c]pyrimidine, imidazo[1,2-a]pyrimidine, imidazo[1,5-a]pyrimidine, imidazo[5,1-b]thiazole, imidazo[2,1-b]thiazole, imidazo[5,1-b]oxazole or imidazo[2,1-b]oxazole.

7. A compound according to claim 3, wherein A is imidazo[1,2-a]pyridine, imidazo[1,5-a]pyridine, imidazo[1,2-c]pyrimidine, imidazo[1,2-a]pyrimidine, imidazo[1,5-a]pyrimidine, imidazo[5,1-b]thiazole, imidazo[2,1-b]thiazole, imidazo[5,1-b]oxazole or imidazo[2,1-b]oxazole.

8. A compound according to claim 4, wherein A is imidazo[1,2-a]pyridine or imidazo[1,2-a]pyrimidine.

9. A compound according to claim 5, wherein A is imidazo[1,2-a]pyridine or imidazo[1,2-a]pyrimidine.

10. A compound according to claim 6, wherein A is imidazo[1,2-a]pyridine or imidazo[1,2-a]pyrimidine.

11. A compound according to claim 1, selected from:

N-([(5S)-N-(4-[imidazo[1,2-a]pyrazin-3-ylcarbonyl]phenyl)-2-oxooxazolidin-5-yl]methyl)acetamide;

N-([(5S)-N-(4-[6-chloroimidazo[1,2-a]pyrimidin-3-ylcarbonyl]phenyl)-2-oxooxazolidin-5-yl]methyl)acetamide;

N-([(5S)-N-(4-[6-(2-hydroxyethylthio)imidazo[1,2-a]pyridin-3-ylcarbonyl]phenyl)-2-oxooxazolidin-5-yl]methyl)acetamide;

N-([(5S)-N-(4-[6-fluoroimidazo[1,2-a]pyridin-3-ylcarbonyl]phenyl)-2-oxooxazolidin-5-yl]methyl)acetamide;

N-([(5S)-N-(4-[imidazo[1,2-a]pyridin-3-ylcarbonyl]{3-fluorophenyl})-2-oxooxazolidin-5-yl]methyl)acetamide;

N-([(5S)-N-(4-[6-chloroimidazo[1,2-a]pyridin-3-ylcarbonyl]phenyl)-2-oxooxazolidin-5-yl]methyl)acetamide;

N-([(5S)-N-(4-[imidazo[2,1-b]thiazol-5-ylcarbonyl]phenyl)-2-oxooxazolidin -5-yl]methyl)acetamide; and N-([(5S)-N-(4-[6-bromoimidazo[1,2-a]pyridin-3-ylcarbonyl]phenyl)-2-oxooxazolidin-5-yl]methyl)acetamide.

12. A pharmaceutical composition comprising:

a compound according to any one of claims 1 through 11; and a pharmaceutically acceptable diluent or carrier.

13. The use of a compound according to any one of claims 1 through 11, for an antibacterial effect in a warm blooded animal.

14. A method for producing an antibacterial effect in a warm blooded animal, in need of such treatment, which comprises administering to said animal an effective amount of a compound according to any one of claims 1 through 11.

15. A process for preparing a compound according to claim 1, comprising the steps of:

a) reacting a compound of formula (II)

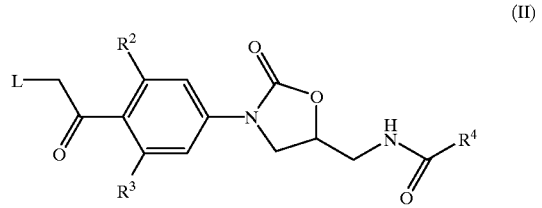

(II)

wherein L is as defined herein, with a compound of formula (III)

(III)

wherein $Y^1$ is a mono- or bicyclic- heteroaryl ring containing at least one nitrogen atom that is capable of quaternizing with (II) and the Me group is adjacent to this nitrogen, in the presence of dimethylformamide dimethylacetal (DMFDMA) (IV)

(IV)

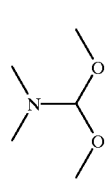

to give a compound of formula (V)

(V)

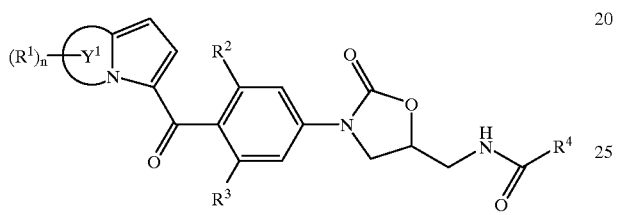

b) reacting a compound of formula (II) with a compound of formula (VI)

(VI)

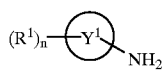

wherein $Y^1$ is as defined above and the $NH_2$ group is adjacent to the nitrogen that is capable of quaternizing with (II), in the presence of DMFDMA (IV) to give a compound of formula (VII)

(VII)

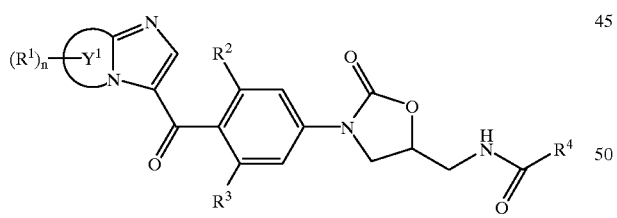

c) reacting a compound of formula (II) with a compound of formula (VIII)

(VIII)

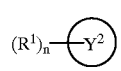

wherein $Y^2$ is a mono- or bicyclic- heteroaryl ring containing at least one nitrogen atom that is capable of quaternizing with (II), followed by reaction with a compound of formula (IX) or an acetylene of formula (IXa)

(IX)

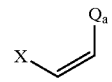

X≡—Q$_a$   (IXa)

wherein X is an electron withdrawing group within the definition of $R^1$ for formula (I) (such as cyano, nitro or $C_{1-4}$alkanoyl) and $Q_a$ is hydrogen or a group within the definition of $R^1$, to give a compound of formula (X)

(X)

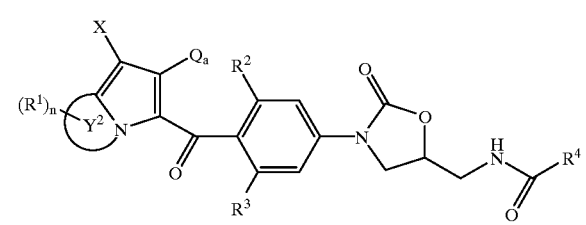

d) reacting a compound of formula (XI)

(XI)

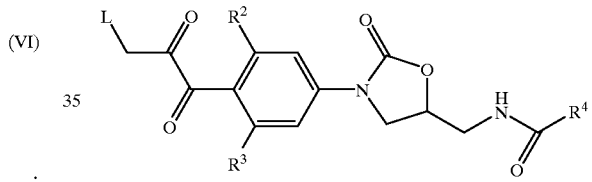

wherein L is as defined above, with a compound of formula (VI) to give a compound of formula (XII)

(XII)

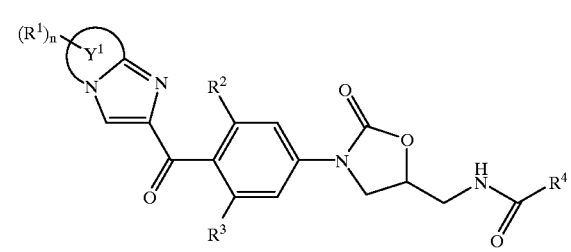

e) reacting a compound of formula (XIII)

(XIII)

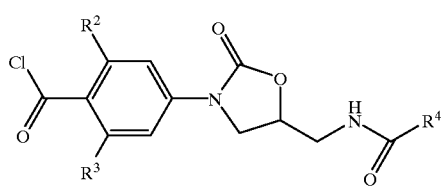

with a compound of formula (XIV)

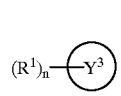
(XIV)

wherein Y³ is a nitrogen-containing 5-membered heteroaryl ring or a nitrogen-containing 5-membered heteroaryl ring fused to a benzo ring which together form a bicyclic heteroaryl ring system without a bridgehead nitrogen, or Y³ is a bicyclic or tricyclic heteroaryl ring system with at least one bridgehead nitrogen, and optionally with a further 1–3 heteroatoms chosen from oxygen, sulfur and nitrogen, to give a compound of formula (XV)

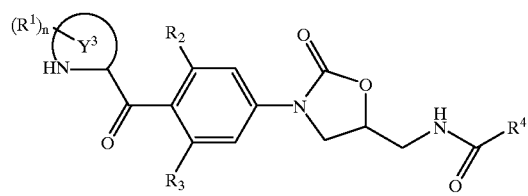
(XV)

f) reacting a compound of formula (XVI)

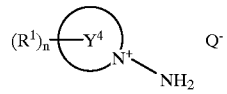
(XVI)

wherein Y⁴ is a mono- or bicyclic- heteroaryl ring containing at least one nitrogen atom that is capable of forming a quaternary complex with the NH₂ group which is attached to this nitrogen and Q is a counter ion, with a compound of formula (XVII)

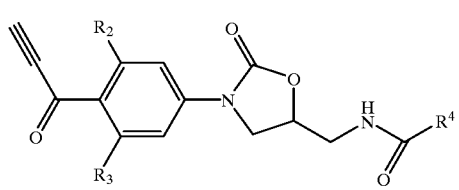
(XVII)

to give a compound of formula (XVIII)

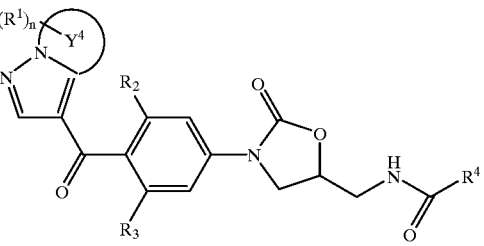
(XVIII)

g) reacting a compound of formula (XIX)

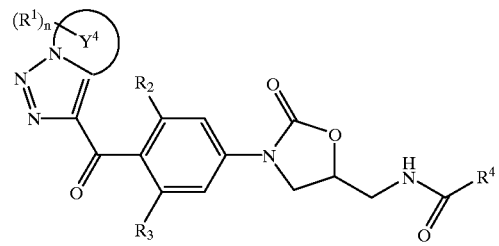
(XIX)

wherein Y⁵ is a mono- or bicyclic- heteroaryl ring containing at least one nitrogen atom that is capable of quaternization, and the —CH₂—C(O)— linking group is adjacent to this nitrogen in the heteroaryl ring, with p-toluenesulfonylazide to give a compound of formula (XX)

(XX)

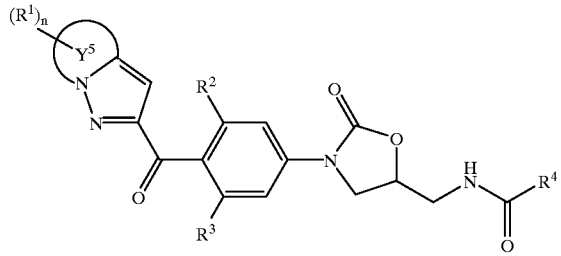

h) reacting a compound of formula (XI) with a compound of formula (XVI) to give a compound of formula (XXI)

(XXI)

or i) for compounds of formula (I) in which A is thiazole or contains a thiazole moiety and is linked via the 2-position of said thiazole, by reaction of a compound of formula (II) with the parent thiazole compound; wherein:

L is chloro, bromo, iodo, triflate or tosylate;

$Y^1$ is a mono- or bicyclic- heteroaryl ring containing at least one nitrogen atom that is capable of quaternizing;

$Y^2$ is a mono- or bicyclic- heteroaryl ring containing at least one nitrogen atom that is capable of quaternizing;

$Y^3$ is a nitrogen-containing 5-membered heteroaryl ring or a nitrogen-containing 5-membered heteroaryl ring fused to a phenyl ring or $Y^3$ is a bicyclic or tricyclic heteroaryl ring system with at least one bridgehead nitrogen, and optionally with a further 1–3 heteroatoms chosen from oxygen, sulfur and nitrogen;

$Y^4$ is a mono- or bicyclic- heteroaryl ring containing at least one nitrogen atom that is capable of quaternizing;

$Y^5$ is a mono- or bicyclic- heteroaryl ring containing at least one nitrogen atom that is capable of quaternizing;

Q is a counter ion;

X is an electron withdrawing group; and $Q_a$ is hydrogen or a group within the definition of $R^1$; and thereafter if necessary i) forming a pharmaceutically acceptable salt, ii) forming an in vivo hydrolysable ester or iii) forming a suitable N-oxide; and when an optically active form of a compound of the formula (I) is required, it may be obtained by carrying out one of the aforesaid procedures using an optically active starting material or by resolution of a racemic form of said compound using a conventional procedure.

* * * * *